US012670998B2

(12) United States Patent
Giddens et al.

(10) Patent No.:    US 12,670,998 B2
(45) Date of Patent:      Jun. 30, 2026

(54) NONINVASIVE DETERMINATION OF RESTING STATE DIASTOLE HEMODYNAMIC INFORMATION

(71) Applicant: COVANOS, INC., Atlanta, GA (US)

(72) Inventors: Don P. Giddens, Hilton Head Island, SC (US); Adrien Lefieux, Montigny-les-Metz (FR); David Molony, Atlanta, GA (US); Alessandro Veneziani, Decatur, GA (US); Alexander Viguerie, Decatur, GA (US); Habib Samady, Atlanta, GA (US); Joo Myung Lee, Johns Creek, GA (US)

(73) Assignee: COVANOS, INC., Atlanta, GA (US)

( * ) Notice: Subject to any disclaimer, the term of this patent is extended or adjusted under 35 U.S.C. 154(b) by 1221 days.

(21) Appl. No.:    17/420,498

(22) PCT Filed:    Jan. 6, 2020

(86) PCT No.:    PCT/US2020/012435

§ 371 (c)(1),
(2) Date:    Jul. 2, 2021

(87) PCT Pub. No.: WO2020/142789

PCT Pub. Date: Jul. 9, 2020

(65)    Prior Publication Data

US 2022/0084684 A1    Mar. 17, 2022

Related U.S. Application Data

(60) Provisional application No. 62/788,914, filed on Jan. 6, 2019.

(51) Int. Cl.
G16H 50/50    (2018.01)
A61B 5/02    (2006.01)
(Continued)

(52) U.S. Cl.
CPC ......... G16H 50/50 (2018.01); A61B 5/02028 (2013.01); A61B 5/022 (2013.01);
(Continued)

(58) Field of Classification Search
CPC .... G16H 50/50; G16H 50/30; A61B 5/02028; A61B 2576/023
See application file for complete search history.

(56)    References Cited

U.S. PATENT DOCUMENTS 6,236,878 B1    5/2001   Taylor et al.
7,739,090 B2    6/2010   Charbel et al.
(Continued)

FOREIGN PATENT DOCUMENTS

JP         2013534154 A     9/2013
JP         2018501894 A     1/2018
(Continued)

OTHER PUBLICATIONS

Groen, "Atherosclerotic Plaque and Shear Stress in Cartoid Arteries", The Netherlands Heart 21-23, 30-32 Institute, Nov. 10, 2010.
(Continued)

*Primary Examiner* — Benjamin O Dulaney
(74) *Attorney, Agent, or Firm* — Greenberg Traurig, LLP; David J. Dykeman; Jonathan Giroux

(57)    ABSTRACT

A diastole-based hemodynamic index, such as instantaneous wave-free ratio (IWFR), may be calculated noninvasively for a patient by receiving image data respective of an anatomical region of the patient, creating an electronic model of the anatomical region, creating one or more boundary conditions model value sets representative of flow conditions during diastole, calculating one or more pressure drops at a location in the anatomical region, and determin- (Continued)

ing, based on the calculated pressure drop(s) and based on a reference pressure, a hemodynamic index value, such as IWFR, for the location.

15 Claims, 7 Drawing Sheets

(51) Int. Cl.
 *A61B 5/022* (2006.01)
 *G16H 30/20* (2018.01)
 *G16H 50/30* (2018.01)
(52) U.S. Cl.
 CPC ............. *G16H 30/20* (2018.01); *G16H 50/30* (2018.01); *A61B 2576/023* (2013.01)

(56) References Cited

U.S. PATENT DOCUMENTS

| | | | |
|---|---|---|---|
| 7,929,148 B2 | 4/2011 | Kemp | |
| 7,930,014 B2 | 4/2011 | Huennekens et al. | |
| 8,157,742 B2 | 4/2012 | Taylor | |
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,318,414 B2 | 11/2012 | Dancu et al. | |
| 8,321,150 B2 | 11/2012 | Taylor | |
| 8,386,188 B2 | 2/2013 | Taylor et al. | |
| 8,449,465 B2 | 5/2013 | Nair et al. | |
| 8,491,567 B2 | 7/2013 | Magnin et al. | |
| 8,496,594 B2 | 7/2013 | Taylor et al. | |
| 8,523,779 B2 | 9/2013 | Taylor et al. | |
| 8,531,428 B2 | 9/2013 | Glynn et al. | |
| 8,548,778 B1 | 10/2013 | Hart et al. | |
| 8,594,950 B2 | 11/2013 | Taylor | |
| 8,606,530 B2 | 12/2013 | Taylor | |
| 8,630,812 B2 | 1/2014 | Taylor | |
| 8,681,116 B2 | 3/2014 | Merritt et al. | |
| 8,706,457 B2 | 4/2014 | Hart et al. | |
| 8,734,356 B2 | 5/2014 | Taylor | |
| 8,734,357 B2 | 5/2014 | Taylor | |
| 8,754,865 B2 | 6/2014 | Merritt et al. | |
| 8,768,669 B1 | 7/2014 | Hart et al. | |
| 8,768,670 B1 | 7/2014 | Hart et al. | |
| 8,797,155 B2 | 8/2014 | Huennekens et al. | |
| 8,803,837 B2 | 8/2014 | Glynn et al. | |
| 8,812,245 B2 | 8/2014 | Taylor | |
| 8,812,246 B2 | 8/2014 | Taylor et al. | |
| 8,824,752 B1 | 9/2014 | Fonte et al. | |
| 8,831,314 B1 | 9/2014 | Fonte et al. | |
| 8,831,315 B1 | 9/2014 | Fonte et al. | |
| 8,837,860 B1 | 9/2014 | Grady et al. | |
| 8,855,984 B2 | 10/2014 | Hart et al. | |
| 8,861,820 B2 | 10/2014 | Fonte et al. | |
| 8,871,461 B2 | 10/2014 | Blackman et al. | |
| 8,914,264 B1 | 12/2014 | Hart et al. | |
| 8,917,925 B1 | 12/2014 | Grady et al. | |
| 8,923,631 B2 | 12/2014 | Spencer | |
| 8,936,553 B2 | 1/2015 | Stigall et al. | |
| 8,958,623 B1 | 2/2015 | Grady et al. | |
| 8,958,863 B2 | 2/2015 | Huennekens et al. | |
| 8,977,336 B2 | 3/2015 | Huennekens et al. | |
| 9,002,690 B2 | 4/2015 | Hart et al. | |
| 9,008,392 B1 | 4/2015 | Bai et al. | |
| 9,008,405 B2 | 4/2015 | Fonte et al. | |
| 9,042,613 B2 | 5/2015 | Spilker et al. | |
| 9,043,190 B2 | 5/2015 | Grady et al. | |
| 9,043,191 B2 | 5/2015 | Grady et al. | |
| RE45,534 E | 6/2015 | Huennekens et al. | |
| 9,055,921 B2 | 6/2015 | Nair et al. | |
| 9,058,692 B1 | 6/2015 | Grady et al. | |
| 9,063,634 B2 | 6/2015 | Hart et al. | |
| 9,063,635 B2 | 6/2015 | Hart et al. | |
| 9,070,214 B1 | 6/2015 | Grady et al. | |
| 9,078,564 B2 | 7/2015 | Taylor et al. | |
| 9,081,721 B1 | 7/2015 | Grady et al. | |
| 9,081,882 B2 | 7/2015 | Taylor et al. | |
| 9,087,147 B1 | 7/2015 | Fonte et al. | |
| 9,121,926 B2 | 9/2015 | Nair et al. | |
| 9,135,699 B2 | 9/2015 | Ralovich et al. | |
| 9,144,417 B2 | 9/2015 | Glynn et al. | |
| 9,149,197 B2 | 10/2015 | Taylor et al. | |
| 9,152,757 B2 | 10/2015 | Taylor et al. | |
| 9,152,761 B2 | 10/2015 | Bhatia et al. | |
| 9,153,047 B1 | 10/2015 | Grady et al. | |
| 9,155,512 B2 | 10/2015 | Choi et al. | |
| 9,159,159 B2 | 10/2015 | Bai et al. | |
| 9,167,974 B2 | 10/2015 | Taylor | |
| 9,168,012 B2 | 10/2015 | Hart et al. | |
| 9,189,600 B2 | 11/2015 | Spilker et al. | |
| 9,195,800 B2 | 11/2015 | Grady et al. | |
| 9,195,801 B1 | 11/2015 | Sankaran et al. | |
| 9,202,010 B2 | 12/2015 | Taylor et al. | |
| 9,220,418 B2 | 12/2015 | Choi et al. | |
| 9,220,419 B2 | 12/2015 | Choi et al. | |
| 9,226,672 B2 | 1/2016 | Taylor et al. | |
| 9,235,679 B2 | 1/2016 | Taylor et al. | |
| 9,239,905 B1 | 1/2016 | Sankaran et al. | |
| 9,262,581 B2 | 2/2016 | Kim et al. | |
| 9,268,902 B2 | 2/2016 | Taylor et al. | |
| 9,271,657 B2 | 3/2016 | Taylor et al. | |
| 9,280,639 B2 | 3/2016 | Sankaran et al. | |
| 9,292,659 B1 | 3/2016 | Grady et al. | |
| 9,292,918 B2 | 3/2016 | Zagrodsky et al. | |
| 9,295,447 B2 | 3/2016 | Shah | |
| 9,304,982 B2 | 4/2016 | Grady et al. | |
| 9,307,926 B2 | 4/2016 | Begin et al. | |
| 9,330,233 B2 | 5/2016 | Bhatia et al. | |
| 9,336,354 B1 | 5/2016 | Sankaran et al. | |
| 9,339,200 B2 | 5/2016 | Fonte et al. | |
| 9,339,348 B2 | 5/2016 | Davies et al. | |
| 9,349,178 B1 * | 5/2016 | Itu .......................... | G16H 50/20 |
| 9,378,580 B2 | 6/2016 | Grady et al. | |
| 9,386,933 B2 | 7/2016 | Grady et al. | |
| 9,390,224 B2 | 7/2016 | Choi et al. | |
| 9,390,232 B2 | 7/2016 | Taylor et al. | |
| 9,424,395 B2 | 8/2016 | Sankaran et al. | |
| 9,424,682 B2 | 8/2016 | Bai et al. | |
| 9,449,145 B2 | 9/2016 | Sankaran et al. | |
| 9,449,146 B2 | 9/2016 | Spilker et al. | |
| 9,449,147 B2 | 9/2016 | Taylor et al. | |
| 9,501,622 B2 | 11/2016 | Sankaran et al. | |
| 9,514,530 B2 | 12/2016 | Grady et al. | |
| 9,517,040 B2 | 12/2016 | Hart et al. | |
| 9,585,623 B2 | 3/2017 | Fonte et al. | |
| 9,585,723 B2 | 3/2017 | Taylor | |
| 9,589,349 B2 | 3/2017 | Grady et al. | |
| 9,594,876 B2 | 3/2017 | Sankaran et al. | |
| 9,607,130 B2 | 3/2017 | Grady et al. | |
| 9,607,386 B2 | 3/2017 | Grady et al. | |
| 9,613,186 B2 | 4/2017 | Fonte et al. | |
| 9,649,171 B2 | 5/2017 | Sankaran et al. | |
| 9,659,375 B2 | 5/2017 | Zagrodsky et al. | |
| 9,668,700 B2 | 6/2017 | Taylor et al. | |
| 9,672,615 B2 | 6/2017 | Fonte et al. | |
| 9,675,301 B2 | 6/2017 | Fonte et al. | |
| 9,679,374 B2 | 6/2017 | Choi et al. | |
| 9,697,330 B2 | 7/2017 | Taylor | |
| 9,706,925 B2 | 7/2017 | Taylor | |
| 9,743,835 B2 | 8/2017 | Taylor | |
| 9,754,082 B2 | 9/2017 | Taylor et al. | |
| 9,770,303 B2 | 9/2017 | Choi et al. | |
| 9,773,219 B2 | 9/2017 | Sankaran et al. | |
| RE46,562 E | 10/2017 | Huennekens et al. | |
| 9,779,483 B2 | 10/2017 | Cohen et al. | |
| 9,785,746 B2 | 10/2017 | Fonte et al. | |
| 9,785,748 B2 | 10/2017 | Koo et al. | |
| 9,801,689 B2 | 10/2017 | Taylor | |
| 9,805,168 B2 | 10/2017 | Sankaran et al. | |
| 9,805,463 B2 | 10/2017 | Choi et al. | |

(56) References Cited

U.S. PATENT DOCUMENTS

| | | | |
|---|---|---|---|
| 9,805,470 B2 | 10/2017 | Bhatia et al. | |
| 9,814,433 B2 | 11/2017 | Benishti et al. | |
| 9,820,660 B2 | 11/2017 | Ryan et al. | |
| 9,836,840 B2 | 12/2017 | Fonte et al. | |
| 9,839,399 B2 | 12/2017 | Fonte et al. | |
| 9,839,483 B2 | 12/2017 | Sankaran et al. | |
| 9,839,484 B2 | 12/2017 | Taylor | |
| 9,852,504 B2 | 12/2017 | Begin et al. | |
| 9,855,020 B2 | 1/2018 | Nair et al. | |
| 9,855,105 B2 | 1/2018 | Taylor | |
| 9,858,387 B2 | 1/2018 | Lavi et al. | |
| 9,861,284 B2 | 1/2018 | Taylor | |
| 9,864,840 B2 | 1/2018 | Grady et al. | |
| 9,870,634 B2 | 1/2018 | Grady et al. | |
| 9,888,971 B2 | 2/2018 | Taylor | |
| 9,891,044 B2 | 2/2018 | Tu et al. | |
| 9,913,616 B2 | 3/2018 | Fonte et al. | |
| 9,943,233 B2 | 4/2018 | Lavi et al. | |
| 9,965,873 B2 | 5/2018 | Grady et al. | |
| 9,965,891 B2 | 5/2018 | Grady et al. | |
| 9,974,453 B2 | 5/2018 | Fonte et al. | |
| 9,974,616 B2 | 5/2018 | Grady et al. | |
| 9,977,869 B2 | 5/2018 | Lavi et al. | |
| 9,986,938 B2 | 6/2018 | Tu et al. | |
| 9,993,303 B2 | 6/2018 | Sankaran et al. | |
| 10,007,762 B2 | 6/2018 | Grady et al. | |
| 10,010,255 B2 | 7/2018 | Fonte et al. | |
| 10,049,093 B2 | 8/2018 | Grady et al. | |
| 10,052,158 B2 | 8/2018 | Taylor | |
| 10,080,613 B2 | 9/2018 | Taylor | |
| 10,080,614 B2 | 9/2018 | Taylor | |
| 10,092,247 B2 | 10/2018 | Taylor | |
| 10,092,360 B2 | 10/2018 | Taylor | |
| 10,096,104 B2 | 10/2018 | Choi et al. | |
| 10,149,723 B2 | 12/2018 | Taylor | |
| 10,154,883 B2 | 12/2018 | Taylor | |
| 10,159,529 B2 | 12/2018 | Taylor | |
| 10,162,939 B2 | 12/2018 | Taylor et al. | |
| 10,166,077 B2 | 1/2019 | Taylor | |
| 10,169,542 B2 | 1/2019 | Choi et al. | |
| 10,169,543 B2 | 1/2019 | Taylor et al. | |
| 10,170,206 B2 | 1/2019 | Koo et al. | |
| 10,179,030 B2 | 1/2019 | Taylor et al. | |
| 10,210,956 B2 | 2/2019 | Lavi et al. | |
| 10,213,119 B2 | 2/2019 | Grady et al. | |
| 10,236,084 B2 | 3/2019 | Grady et al. | |
| 10,262,101 B2 | 4/2019 | Grady et al. | |
| 10,285,762 B2 | 5/2019 | Sankaran et al. | |
| 10,304,569 B2 | 5/2019 | Grady et al. | |
| 10,307,131 B2 | 6/2019 | Taylor et al. | |
| 10,314,654 B2 | 6/2019 | Sankaran et al. | |
| 10,314,655 B2 | 6/2019 | Grady et al. | |
| 10,321,958 B2 | 6/2019 | Taylor | |
| 10,327,847 B2 | 6/2019 | Taylor | |
| 10,354,349 B2 | 7/2019 | Sankaran et al. | |
| 10,354,759 B2 | 7/2019 | Taylor et al. | |
| 10,376,317 B2 | 8/2019 | Taylor | |
| 10,390,782 B2 | 8/2019 | Klingenbeck et al. | |
| 10,390,885 B2 | 8/2019 | Spilker et al. | |
| 10,395,776 B2 | 8/2019 | Choi et al. | |
| 10,398,386 B2 | 9/2019 | Grady et al. | |
| 10,405,925 B2 | 9/2019 | Jaquet et al. | |
| 10,413,432 B2 | 9/2019 | Grady et al. | |
| 10,420,610 B2 | 9/2019 | Bai et al. | |
| 10,424,063 B2 | 9/2019 | Lavi et al. | |
| 10,433,740 B2 | 10/2019 | Fonte et al. | |
| 10,441,361 B2 | 10/2019 | Taylor | |
| 10,456,094 B2 | 10/2019 | Fonte et al. | |
| 10,463,336 B2 | 11/2019 | Itu et al. | |
| 10,478,252 B2 | 11/2019 | Taylor et al. | |
| 10,492,866 B2 | 12/2019 | Taylor | |
| 10,499,990 B2 | 12/2019 | Grady et al. | |
| 10,517,677 B2 | 12/2019 | Sankaran et al. | |
| 10,517,678 B2 | 12/2019 | Taylor et al. | |
| 10,522,254 B2 | 12/2019 | Sankaran et al. | |
| 10,531,923 B2 | 1/2020 | Taylor | |
| 10,546,049 B2 | 1/2020 | Grady et al. | |
| 10,546,403 B2 | 1/2020 | Grady et al. | |
| 10,553,317 B2 | 2/2020 | Grady et al. | |
| 10,561,324 B2 | 2/2020 | Fonte et al. | |
| 10,572,998 B2 | 2/2020 | Bhatia et al. | |
| 10,575,810 B2 | 3/2020 | Sankaran et al. | |
| 10,595,728 B2 | 3/2020 | Choi et al. | |
| 10,595,807 B2 | 3/2020 | Lavi et al. | |
| 10,600,181 B2 | 3/2020 | Peterson et al. | |
| 10,607,739 B2 | 3/2020 | Grady et al. | |
| 10,622,092 B2 | 4/2020 | Kim et al. | |
| 10,682,180 B2 | 6/2020 | Taylor | |
| 10,682,183 B2 | 6/2020 | Grady et al. | |
| 10,692,608 B2 | 6/2020 | Koo et al. | |
| 10,702,339 B2 | 7/2020 | Taylor | |
| 10,702,340 B2 | 7/2020 | Taylor | |
| 10,716,513 B2 | 7/2020 | Choi et al. | |
| 10,719,931 B2 | 7/2020 | Fonte et al. | |
| 10,776,988 B2 | 9/2020 | Grady et al. | |
| 10,786,308 B2 | 9/2020 | Sankaran et al. | |
| 10,789,706 B2 | 9/2020 | Grady et al. | |
| 10,803,592 B2 | 10/2020 | Grady et al. | |
| 10,842,568 B2 | 11/2020 | Hart et al. | |
| 10,854,339 B2 | 12/2020 | Grady et al. | |
| 10,867,707 B2 | 12/2020 | Grady et al. | |
| 10,874,461 B2 | 12/2020 | Jaquet et al. | |
| 10,878,963 B2 | 12/2020 | Taylor et al. | |
| 10,881,465 B2 | 1/2021 | Grady et al. | |
| 10,939,828 B2 | 3/2021 | Fonte et al. | |
| 10,939,960 B2 | 3/2021 | Choi et al. | |
| 10,945,606 B2 | 3/2021 | Sanders et al. | |
| 10,951,715 B2* | 3/2021 | Hart | H04N 1/00506 |
| 10,964,071 B2 | 3/2021 | Grady et al. | |
| 10,966,619 B2 | 4/2021 | Fonte et al. | |
| 10,973,583 B2 | 4/2021 | Taylor et al. | |
| 10,978,210 B2 | 4/2021 | Grady et al. | |
| 10,984,535 B2 | 4/2021 | Grady et al. | |
| 10,987,010 B2 | 4/2021 | Grady et al. | |
| 10,990,652 B2 | 4/2021 | Taylor et al. | |
| 10,991,465 B2 | 4/2021 | Grady | |
| 11,013,425 B2 | 5/2021 | Fonte et al. | |
| 11,017,904 B2 | 5/2021 | Sankaran et al. | |
| 11,033,332 B2 | 6/2021 | Taylor | |
| 11,042,822 B2 | 6/2021 | Sankaran et al. | |
| 11,083,524 B2 | 8/2021 | Taylor | |
| 11,087,884 B2 | 8/2021 | Sankaran et al. | |
| 11,090,118 B2 | 8/2021 | Taylor | |
| 11,116,575 B2 | 9/2021 | Taylor | |
| 11,120,893 B2 | 9/2021 | Choi et al. | |
| 11,127,503 B2 | 9/2021 | Rabbat et al. | |
| 11,135,012 B2 | 10/2021 | Taylor | |
| 11,138,337 B2 | 10/2021 | Yousfi et al. | |
| 11,813,104 B2* | 11/2023 | Samady | G06T 17/20 |
| 2006/0223047 A1 | 10/2006 | Dancu et al. | |
| 2006/0235669 A1 | 10/2006 | Charbel et al. | |
| 2011/0059480 A1 | 3/2011 | Blackman et al. | |
| 2011/0142316 A1 | 6/2011 | Wang et al. | |
| 2013/0243294 A1 | 9/2013 | Ralovich et al. | |
| 2014/0058715 A1 | 2/2014 | Sharma et al. | |
| 2014/0200867 A1 | 7/2014 | Lavi et al. | |
| 2014/0379318 A1 | 12/2014 | Spilker et al. | |
| 2015/0238121 A1 | 8/2015 | Tu et al. | |
| 2015/0265162 A1 | 9/2015 | Lavi et al. | |
| 2015/0297161 A1 | 10/2015 | Grass et al. | |
| 2015/0324962 A1* | 11/2015 | Itu | G16H 30/40 |
| | | | 382/130 |
| 2015/0335304 A1 | 11/2015 | Lavi et al. | |
| 2015/0342551 A1 | 12/2015 | Lavi et al. | |
| 2016/0000341 A1 | 1/2016 | Rotman et al. | |
| 2016/0247279 A1 | 8/2016 | Lavi et al. | |
| 2017/0007332 A1 | 1/2017 | Spilker et al. | |
| 2017/0046834 A1 | 2/2017 | Itu et al. | |
| 2017/0220760 A1 | 8/2017 | Fonte | |
| 2017/0245821 A1 | 8/2017 | Itu et al. | |
| 2017/0258431 A1 | 9/2017 | Klingenbeck et al. | |
| 2017/0364658 A1 | 12/2017 | Lavi et al. | |
| 2018/0032653 A1 | 2/2018 | Aben et al. | |
| 2018/0089829 A1* | 3/2018 | Zhong | G06T 11/003 |

(56) References Cited

U.S. PATENT DOCUMENTS

| | | | | |
|---|---|---|---|---|
| 2018/0140258 A1* | 5/2018 | Fonte | ..................... | A61B 6/504 |
| 2018/0174490 A1* | 6/2018 | Randles | .............. | G09B 23/303 |
| 2018/0271468 A1* | 9/2018 | Goshen | ................ | G06T 7/0012 |
| 2018/0368916 A1* | 12/2018 | Taylor | ............... | A61B 5/02007 |
| 2020/0352536 A1 | 11/2020 | Samady et al. | | |
| 2022/0101520 A1 | 3/2022 | Giddens et al. | | |

FOREIGN PATENT DOCUMENTS

| | | | |
|---|---|---|---|
| WO | WO 2006010609 A2 | 2/2006 | |
| WO | 2015153362 A1 | 10/2015 | |
| WO | WO 2017200381 A1 | 11/2017 | |
| WO | 2018226999 A | 12/2018 | |
| WO | WO 2019071249 A1 | 4/2019 | |

OTHER PUBLICATIONS

Tesche et al., "Coronary CT Angiography-Derived Fractional Flow Reserve", Radiology, vol. 285, No. 1, pp. 17-33, Oct. 2017.

Xiao et al., "A Systematic Comparison Between 1-D and 3-D Hemodynamics in Compliant Arterial Models", International Journal for Numerical Methods in Biomedical Engineering, vol. 30, pp. 204-231, Feb. 2014.

European Extended Search Report; EP20735946.4; Date: Sep. 2, 2022.

International Search Report and Written Opinion in PCT International Patent Application No. PCT/US2020/012435 mailed Mar. 31, 2020 (12 pages).

Uus et al. "Patient-Specific Blood Flow Modelling in Diagnosis of Coronary Artery Disease" Thesis Dissertation, Department of Electrical and Electronic Engineering, City University, Loondon, 2016.

* cited by examiner

58

NONINVASIVE DETERMINATION OF RESTING STATE DIASTOLE HEMODYNAMIC INFORMATION

CROSS-REFERENCE TO RELATED APPLICATION

This application is a U.S. national phase application of PCT International Patent Application No. PCT/US2020/012435, filed Jan. 6, 2020 which claims the benefit of and priority to U.S. Provisional Application No. 62/788,914, filed Jan. 6, 2019, the entire contents of each of which are incorporated herein by reference.

FIELD

This disclosure is generally directed to determination and display of patient hemodynamic information based on non-invasive imaging and computational fluid dynamics, including determination and display of resting state diastole-based hemodynamic information, such as instantaneous wave-free ratio (IWFR).

BACKGROUND

Coronary heart disease (CHD) is the most common cause of death in the U.S., with estimated direct and indirect annual costs of hundreds of billions of dollars. CHD results from atherosclerosis, which can progress and lead to ischemia, angina, myocardial infarction and death. Various treatment options, including medical therapy, intravascular stents, and coronary artery bypass graft (CABG) surgery, can be provided to a patient depending upon the severity and complexity of the patient's lesions and clinical status. A typical diagnostic and treatment plan includes clinical evaluation, non-invasive stress testing and, for appropriate patients, invasive coronary angiography and subsequent medical therapy and/or coronary revascularization. Typically, if the patient remains symptomatic on medical therapy or a significant defect is found in myocardial perfusion, the care provider will perform an invasive coronary angiography on the patient. In such patients, the decision to revascularize or not using coronary stents or CABG surgery is made based on angiographic anatomical findings and, increasingly, with use of hemodynamic information, such as invasively-measured fractional flow reserve (FFR). Measurement of FFR in the catheterization laboratory requires inserting a pressure wire into the patient's coronary arteries, and an FFR value of less than 0.8 is generally considered to be indicative of a clinically-significant obstructive lesion warranting revascularization in the appropriate clinical context.

Instantaneous wave-free ratio (IWFR) is a hemodynamic index that has been shown to have comparable diagnostic accuracy to FFR for determining obstructive coronary artery lesions). Like FFR, IWFR is measured invasively using a pressure wire. Also like FFR, IWFR is defined as the ratio of intravascular pressure distal to a lesion(s) (Pd) to the pressure in the aorta (Pa). IWFR differs from FFR in several ways. First, while FFR requires the induction of hyperemia when measuring the pressure ratio, IWFR does not. As a result, FFR includes a more complicated measurement procedure than does IWFR, which is measured under resting conditions. Second, FFR uses pressures averaged over a cardiac cycle, while IWFR employs pressure measurements averaged during a so-called wave-free period of diastole in which the resistance to flow is approximately constant at a minimal value.

IWFR is not the only hemodynamic parameter measured under resting conditions during diastole. Other pressure ratio indices measured under resting conditions during diastole include diastolic pressure ratio (dPR), which averages the ratio over 25% to 75% of the diastolic period, and the pressure ratio measured at the midpoint of diastole (dPR$_{mid}$), both of which have been shown to have diagnostic accuracy comparable to IWFR.

SUMMARY

Noninvasive determination of resting state diastole hemodynamic information is disclosed herein. A first example method for providing hemodynamic information respective of a patient may include obtaining a three-dimensional electronic model of a coronary artery of the patient and obtaining a boundary condition model value set that is representative of a diastole period of the patient's cardiac cycle at a resting state of the patient. The method may further include performing a three-dimensional computational fluid dynamics (CFD) simulation of the coronary artery model based on the boundary condition model value set, and calculating, according to the CFD simulation, a pressure drop between a first location of the coronary artery and a second location of the coronary artery. The method may further include determining, based on the calculated pressure drop and based on a reference pressure, a hemodynamic index value indicative of the presence of a lesion at the location.

In an embodiment of the first example method, the boundary condition model value set is representative of an entire diastole period of the patient's cardiac cycle.

In an embodiment of the first example method, the boundary condition model value set is representative of a diastolic wave free period of the patient's cardiac cycle.

In an embodiment of the first example method, the boundary condition model value set is representative of a mid-diastole point of the patient's cardiac cycle.

In an embodiment of the first example method, the method further comprises creating the electronic model of the anatomical region.

In an embodiment of the first example method, the method further comprises receiving image data respective of the anatomical region of the patient, and creating the electronic model based on the received image data.

In an embodiment of the first example method, the boundary condition model value set comprises an inlet flow rate at an inlet of the coronary artery that is representative of a resting state of the patient, and two or more outlet flow rates calculated according to the inlet flow rate and a flow splitting model.

In an embodiment of the first example method, the method further comprises calculating the flow splitting model according to a geometry of the three dimensional model of the coronary artery, and calculating the two of more outlet flow rates according to the inlet flow rate and a flow splitting model.

An example embodiment of a system for providing hemodynamic information respective of a patient may include a non-transitory, computer-readable memory storing instructions and a processor configured to execute the instructions to obtain a three-dimensional electronic model of a coronary artery of the patient and obtain a boundary condition model value set that is representative of a diastole period of the patient's cardiac cycle at a resting state of the patient. The processor may be configured to execute the instructions further to perform a three-dimensional computational fluid dynamics (CFD) simulation of the coronary artery model based on the boundary condition model value set, calculate, according to the CFD simulation, a pressure drop between a first location of the coronary artery and a second location of the coronary artery, and determine, based on the calculated pressure drop and based on a reference pressure, a hemodynamic index value indicative of the presence of a lesion at the location.

In an embodiment of the example system, the boundary condition model value set is representative of an entire diastole period of the patient's cardiac cycle.

In an embodiment of the example system, the boundary condition model value set is representative of a diastolic wave free period of the patient's cardiac cycle.

In an embodiment of the example system, the boundary condition model value set is representative of a mid-diastole point of the patient's cardiac cycle.

In an embodiment of the example system, the memory stores further instructions that, when executed by the processor, cause the processor to create the electronic model of the anatomical region.

In an embodiment of the example system, the memory stores further instructions that, when executed by the processor, cause the processor to receive image data respective of the anatomical region of the patient, and create the electronic model based on the received image data.

In an embodiment of the example system, the boundary condition model value set comprises an inlet flow rate at an inlet of the coronary artery that is representative of a resting state of the patient, and two or more outlet flow rates calculated according to the inlet flow rate and a flow splitting model.

In an embodiment of the example system, the memory stores further instructions that, when executed by the processor, cause the processor to calculate the flow splitting model according to a geometry of the three dimensional model of the coronary artery, and calculate the two of more outlet flow rates according to the inlet flow rate and a flow splitting model.

A second example method for providing hemodynamic information respective of a patient may include obtaining a three-dimensional electronic model of an anatomical region of the patient, obtaining a boundary condition model that is representative of a resting state of the patient, and calculating, based on the three-dimensional model and the boundary condition model, at a first time point in a cardiac cycle of the patient, a first pressure drop across a portion of an anatomical region of a patient. The second example method may further include calculating, based on the three-dimensional model and the boundary condition model, at a second time point in a cardiac cycle of the patient that is different than the first time point, a second pressure drop across the anatomical region portion, calculating, for a range of time points of the cardiac cycle of the patient, respective pressure drops across the region according to the first and second pressure drops, and determining, based on the calculated pressure drops for the range of time points and based on a reference pressure, a hemodynamic index value indicative of the presence of a lesion at the location.

In an embodiment of the second example method, the anatomical region is a blood vessel, and the anatomical region portion extends from an inlet of the blood vessel to a location in the artery.

In an embodiment of the second example method, the anatomical region is a coronary artery.

In an embodiment of the second example method, the method further comprises receiving image data respective of the anatomical region of the patient, and creating the electronic model based on the received image data.

DETAILED DESCRIPTION

Figure 1:
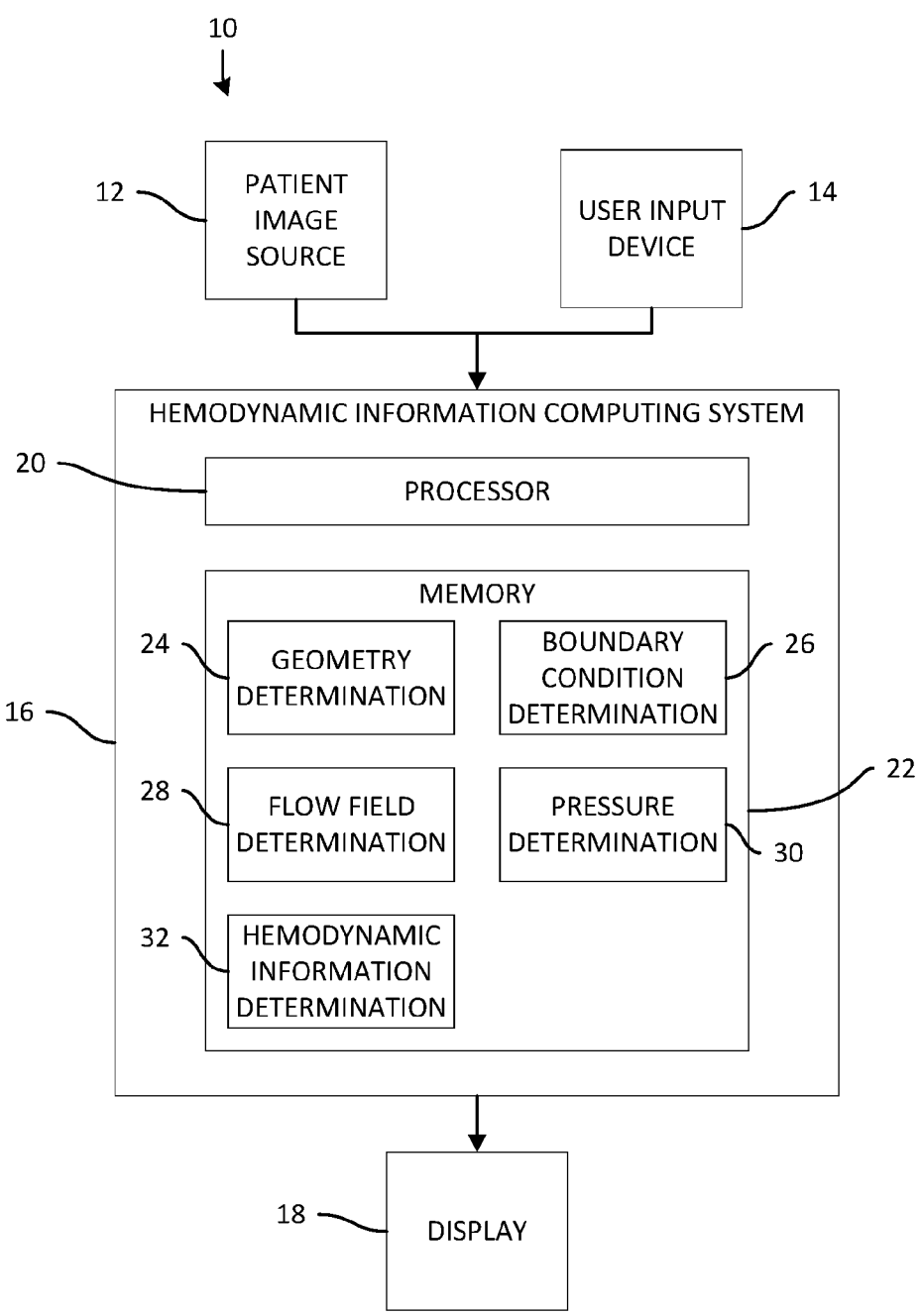
FIG. 1 is a diagrammatic view of an example embodiment of an electronic system for determining hemodynamic information of a patient.

Given the diagnostic accuracy of invasive IWFR and other diastolic pressure ratio indices, a method for computing these using noninvasive imaging and computational hemodynamics would be beneficial as a tool in selecting those patients who should, or should not, proceed to invasive diagnostic angiography. Because known hemodynamic indices, such as FFR, dPR, and IWFR, are measured invasively, and because approximately fifty percent of patients who undergo such invasive measurements are not found to have obstructive disease, there is a clinical need for a noninvasive diagnostic method of determining IWFR and similar diastolic indices as a screening tool.

Noninvasively-captured image data, such as CT images, and computational fluid dynamics (CFD) may be used to rapidly compute the hemodynamic relationship between pressure and coronary artery flow over a range of anticipated blood flow requirements that a specific individual is likely to experience in daily activity. Using this relationship, specific indices of intra-arterial pressure losses, including IWFR and other diastolic pressure ratios that describe the degree of flow obstruction caused by coronary artery disease can be computed noninvasively. Coupled with other clinically derived information, a determination whether invasive diagnostic procedures or interventions are advisable can be made.

Current approaches to computed FFR assume hyperemic flow, which requires an assumption on the increase in flow from resting to hyperemic conditions for a specific individual. This flow increase depends on the pathophysiologic state of the individual and may vary from a factor as large as 4 or 5 to a factor as little as slightly over 1, depending on the individual. Thus, using an assumed resting flow (as is required for IWFR) as opposed to an assumed hyperemic flow (for FFR) may reduce uncertainty in the assumed inflow conditions for CFD, and thus may provide improved accuracy relative to CFD-based FFR.

Individuals vary in resting flow demand depending on their physical state and metabolic requirements. Estimating resting flow for a potentially diseased population may have less variability than estimating flow under hyperemic conditions due to underlying pathophysiology, e.g. microvascular disease and other factors. Basing a decision to recommend an invasive diagnostic procedure using computations based on hyperemic flow conditions may not be appropriate for the population at large. The present disclosure provides a noninvasive computational approach to simulate a pressure drop during diastolic flow to give important diagnostic information.

The present disclosure may further provide improvements over known CFD-based FFR calculation methods by accounting for patient-specific metabolic needs. In some embodiments, a more accurate CFD-based IWFR value can be computed for a patient by incorporating information from the patient's daily metabolic activity. This patient-specific metabolic workload information may be used to inform the flow rates utilized in the IWFR calculations.

IWFR and other hemodynamic indices may be calculated based on flow fields in the patient's vasculature, which may be based on the Navier-Stokes equations of fluid motion. The Navier-Stokes equations can be employed to describe the flow field in a coronary artery, e.g., intravascular pressures and velocities in a region of interest (ROI), as functions of time and three-dimensional (3D) space, in some forms, and solely of 3D space in other forms. From these flow fields, quantities of clinical interest can be computed such as, for example, pressure drop, FFR, instantaneous wave-free ratio (IWFR), other diastolic pressure indices, forces on artery walls caused by intravascular pressure variations and viscous shearing stresses (wall shear stress (WSS)), etc. In order to solve the Navier-Stokes equations, CFD is employed, and the solution includes imposing boundary conditions for the ROI. The subject's vessel lumen geometry (obtained from CT or other imaging) is also included in CFD, along with some combination of inflow rate (e.g., at a selected inflow boundary) and flow distribution among vessel branches (e.g., one or more outflows). The pressure field in the ROI may be computed as a deviation from a reference pressure, and thus the absolute level of pressure, e.g., Pa, in the ROI may not be needed at the time of calculation of the pressure field. Once the deviations from reference are computed, the absolute pressures in the field can be determined when the reference pressure (e.g., Pa) is determined.

For many clinical applications in coronary artery flows, such as pressure drop, FFR, and IWFR, the Navier-Stokes equations may be treated as independent of time (i.e., in three spatial dimensions, but independent of the time dimension). For example, the time average of the pressure ratio, Pd/Pa, is representative of the average of the instantaneous pressure ratio, where Pd is the pressure in the ROI and Pa is the reference pressure. This means that a three-dimensional CFD model is appropriate for computing these pressure indices, thus enabling a faster computation than a four-dimensional model (i.e., a model that incorporates three spatial dimensions and time).

A pressure field within a ROI may be determined based on, e.g., flow rates in and around the ROI. For coronary artery flow and pressure, the relationship between flow rate and pressure gradient ($\Delta P$) between a proximal location and distal location in the region of interest can be approximated well by a quadratic equation, shown as equation (1) below:

$$\Delta P = aQ + bQ^2 \qquad \text{(Eq. 1)}$$

where a and b are constants that depend upon the vessel geometry and blood viscosity of an individual patient, and which may be calculated for a given patient in the manner described below. Equation (1) has both a physical and mathematical basis. Physically, the aQ term is related to pressure losses directly due to blood viscosity, while the $bQ^2$ term is related to pressure losses arising from flow separation and, if present, turbulence. The $bQ^2$ term may be significant when a stenosis is sufficiently great to cause flow separation. Mathematically, the equation can be viewed as the first two terms in a polynomial series expansion for $\Delta P = fcn(Q)$. Equation (1) solves for the pressure drop across a region of a subject patient's vasculature for which a flow field is determined via computational fluid dynamics.

In order to compute a and b, the three-dimensional Navier-Stokes equations for two values of Q may be solved. For example, a first value, $Q_1$, may represent a flow rate for the beginning of diastole (or another time point) and a second value, $Q_2$, may represent a flow rate for the end of diastole (or another time point). In other embodiments, the $Q_1$ may be representative of a first physiologic state and $Q_2$ may be representative of a different, second, physiologic state. These computations will give two values for $\Delta P$ so that the equations (2) and (3), below, may be solved for a and b once $Q_1$, $Q_2$, $\Delta P_1$ and $\Delta P_2$ are known:

$$\Delta P_1 = aQ_1 + bQ_1^2 \qquad \text{(Eq. 2)}$$

$$\Delta P_2 = aQ_2 + bQ_2^2 \qquad \text{(Eq. 3)}$$

Once coefficients a and b are known for a given patient, it is possible to compute $\Delta P$ over a range of flow conditions (e.g., a range of physiologically relevant flow conditions) without further CFD for each flow condition in the range.

The clinical definition for IWFR is shown in equation (4) below:

$$\text{IWFR} = Pd/Pa \qquad \text{(Eq. 4)}$$

where Pd and Pa are the distal coronary artery and aortic pressures, respectively, averaged during the wave free period of diastole. Alternatively, IWFR can be defined using the wave free period values, as shown in equation (5) below:

$$\text{IWFR} = 1 - \Delta P/Pa \qquad \text{(Eq. 5)}$$

Equations (4) and (5) may also be applied to calculate other indices by calculating Pd and Pa (for equation (4)) or $\Delta P$ and Pa (for equation (5)) at different portions or points of the cardiac cycle. For example, diastolic pressure ratio (dPR) may be calculated by performing calculations for the entirety of diastole.

Once $Q_1$ and $Q_2$ are determined (in order to determine $\Delta P$ at the beginning and end of the wave-free period of diastole, respectively, for IWFR), and Pa is determined for the beginning and end of the wave-free period of diastole, an IWFR value may then be calculated. For example, in an embodiment, a pressure v. flow rate curve may be calculated for diastole, and that curve may be integrated and averaged to calculate an IWFR value noninvasively.

As discussed above, an IWFR value may be computed by performing CFD under two different conditions (e.g., two different points in the cardiac cycle). Alternatively, in an embodiment, a single computation may be performed to calculate IWFR noninvasively based on a single representative Q value and a single representative Pa value for a wave-free period of diastole. The representative Q value may be calculated according to a geometry of the anatomical region of interest, in some embodiments (as discussed below with respect to equation (9)).

As noted above, one or more Pa values are required as reference pressures for an IWFR calculation. In an embodiment, brachial cuff pressure measurements can be used to estimate the mean diastolic pressure. Cuff pressures provide peak systolic pressure (SP) and minimum diastolic pressure (DP). The resting mean aortic diastolic pressure ($Pa_{dmean}$, or dPa)—which may be used for an IWFR calculation—during the wave free period may be estimated from cuff values of SP and DP according to the transfer function set forth in the following equation 6, in some embodiments:

$$Pa_{dmean} = (SP + 3DP)/4 \qquad \text{(Eq. 6)}$$

In other embodiments, other transfer functions may be used to relate a cuff pressure values to a reference pressure.

In another embodiment, the resting mean aortic diastolic pressure Pa ($Pa_{dmean}$, or dPa) may be calculated from a cuff pressure as shown in equation 7 below:

$$dPa = Pc + \text{offset} \qquad \text{(Eq. 7)}$$

where Pc is the resting brachial cuff pressure given by equation 8 below:

$$Pc = dPc + FF^*PP \qquad \text{(Eq. 8)}$$

where dPc is the diastolic cuff pressure, FF is a scalar form factor, and PP is the cuff pulse pressure (e.g., the difference between the systolic (SP) and diastolic (DP) cuff pressures of the subject patient at rest). The scalar form factor FF may have a value of between 0.15 and 0.45, and may depend patient-specific characteristics, including heart rate, age, height, systolic pressure, and/or augmentation index, for example. In some embodiments, FF may be approximately 0.2, 0.25, or 0.33. In some embodiments, the offset value of equation 7 may be between about zero (0) and –10 mmHg. In an embodiment, the offset value of equation 7 may be about –7 mmHg. The value of the offset may depend on the value of the form factor FF, the desired hemodynamic index (and, therefore, the portion of the cardiac cycle under examination), and the physiological state of the patient, in some embodiments.

In other embodiments, the mean aortic diastolic pressure may be estimated using a transfer function that relates cuff pressures to aortic pressures during diastole. For example, the diastolic Pa value may be determined from a cuff pressure of the subject patient by finding a value of form factor FF and/or an offset value that fits a data set including invasively measured cuff pressures and diastolic resting central pressures of a patient population. Once this function is known, it can be used to obtain an estimate of the diastolic resting pressures from non-invasively measured cuff pressures.

In another embodiment, the mean aortic diastolic pressure may be estimated from a combination of an optical finger device or other wearable pressure measurement device (e.g., a radial tonometry device) and a brachial cuff pressure device. For example, a Fourier analysis of the optical finger device output may be performed and mathematically combined with the brachial cuff pressure to determine a value of Pa.

Referring to the drawings, wherein like reference numerals refer to the same or similar features in the various views, FIG. 1 is a diagrammatic view of an example embodiment of an electronic system 10 for determining hemodynamic information. The example system 10 may include a patient image source 12, a user input device 14, a hemodynamic information computing system 16, and a display 18. As will be described in greater detail below, the system 10 may find use in calculating hemodynamic information of a patient based on electronic patient data (e.g., images of a region of interest of the patient and other data), and/or to make a recommendation regarding further testing (e.g., further non-invasive or interventional evaluation) and/or interventional therapy for the patient based on the determined hemodynamic information.

One or more aspects of the system 10 may be deployed in a clinical environment, in an embodiment. For example, in some embodiments, the patient image source 12, user input device 14, hemodynamic information computing system 16, and the display 18 may all be provided in a common clinical setting, such as a hospital. In some embodiments, the components of the system 10 may be embodied in a laptop or desktop computer or workstation. In some embodiments, some components of the system 10—such as the hemodynamic information computing system 16—may be remote from the clinical setting, such as in a cloud computing-based implementation.

The patient image source 12 may include a medical image acquisition device configured to acquire one or more medical images of a vascular system of a subject patient. For example, the patient image source 12 may be a noninvasive image acquisition device. In some embodiments, the patient image source 12 may include but is not limited to a computed tomography (CT) acquisition device, intravascular ultrasound (IVUS), biplane angiography, optical coherence tomography (OCT), magnetic resonance imaging (MRI), among others, or a combination thereof.

Additionally or alternatively, the patient image source 12 may include a store of existing image data of the subject patient. In some embodiments, patient image source 12 may include a medical image storage device, such as a database or other local electronic data storage, or a remote storage (e.g., cloud-based storage) configured to store medical images.

The user input device 14 may be or may include one or more devices for input to a computing system, such as a mouse, touchpad, touchscreen, keyboard, microphone, camera, or other input device.

The hemodynamic information computing system 16 may include a processor 20 and a non-transitory, computer-readable memory 22 configured to store data and instructions. In an embodiment, the memory 22 may store images from a subject patient, and thus may serve as the patient image source 12, or an aspect thereof. The processor 20 may be configured to execute instructions stored in the memory 22 to perform one or more of the steps, methods, algorithms, etc. of this disclosure. In particular, the memory 22 may be configured to store various functional modules in the form of instructions, including a geometry determination module 24, a boundary condition determination module 26, a flow field determination module 28, a pressure determination module 30, and a hemodynamic information determination module 32.

The various modules 24, 26, 28, 30, 32 in the memory 22 will be described separately, but it should be understood that such separation is for ease of discussion only. The instructions in which the various modules are embodied may be in common files, storage devices, etc. and, similarly, one or more of the modules described herein may be separated into multiple separate files, storage devices, etc.

The geometry determination module 24 may be configured to generate an electronic geometrical representation (e.g., model) of an anatomical region of interest (ROI) from images obtained from the patient image source. In some embodiments, the ROI may be a portion of the subject patient's cardiovascular system, such as one or more arterial segments. The one or more arterial segments may include a portion of one or more arteries and one or more branches that extend therefrom.

In some embodiments, the one or more arterial segments may include one or more coronary arterial segments. The one or more coronary arterial segments may include a portion of one or more coronary arteries emanating from an aorta of a subject and one or more branches that extend therefrom. The one or more coronary arterial segments may include but is not limited to one or more portions of the left coronary artery (LCA) and/or the right coronary artery (RCA). The one or more coronary arterial segments for the left coronary artery (LCA) may include but is not limited the left main coronary artery (LM), the left anterior descending (LAD), the left circumflex artery (also referred to as the "Circumflex"), among others, or a combination thereof.

The disclosure will make reference to coronary arterial segments. However, it will be understood that the one or more arterial segments are not limited to the coronary arterial segments discussed and may include other coronary arterial segments, other types of arterial segments, among others, or a combination thereof. For example, the one or more arterial segments may include cerebral arterial segment(s), femoral arterial segment(s), iliac arterial segment(s), popliteal arterial segment(s), carotid arterial segment(s), renal artery segment(s), and the like.

In some embodiments, the geometrical representation produced by the geometry determination module 24 may be a three-dimensional (3D) electronic model of the spatial volume of one or more arterial segments. For example, the geometrical representation of one or more arterial segments may be discretized into a three-dimensional volumetric mesh, for example, polyhedrons (e.g., tetrahedrons). In some embodiments, the geometrical representation may include a surface mesh representing the boundary of the lumens of each arterial segment.

In some embodiments, the boundary condition determination module 26 may be configured to determine boundaries for each arterial segment. "Boundaries" may refer to cross-sections of the representation of the arterial segment and may include but are not limited to: inflow boundary corresponding to the cross-section through which the blood flows; one or more outflow boundaries corresponding to the cross-section disposed downstream or distal from the inflow boundary through which blood flow is directed outward; one or more vessel wall boundaries corresponding to an interface between the inner surface of the arterial wall and the flowing blood; among others; or combination thereof.

In some embodiments, the one or more outflow boundaries may include an outflow boundary disposed at or adjacent to a junction point (e.g., bifurcation, trifurcation, and the like, and combinations thereof). In some embodiments, the one or more outflow boundaries may include an outflow boundary disposed at or adjacent to the left Circumflex artery. In some embodiments, the one or more outflow boundaries may include a first outflow boundary and a second outflow boundary that is disposed between the inflow boundary and the first outflow boundary. In some embodiments, the first outflow boundary may correspond to a distal boundary of the segment (i.e., the cross-section disposed downstream or distal from the inflow boundary). In some embodiments, for example, when the geometrical representation includes the left coronary artery, the second outflow boundary may correspond to the circumflex. In some embodiments, the first outflow boundary and the second outflow boundary may be separated by one or more additional outflow boundaries, for example, at least a third outflow boundary. The third outflow boundary may correspond to or be adjacent to a junction point, such as a branch or bifurcation.

In some embodiments, the boundary condition determination module 26 may be configured to determine geometrical data for each boundary using the geometric representation generated by the geometry determination module 24. In some embodiments, the geometrical data may include but is not limited to vessel radius, diameter, circumference, length, area, epicardial coronary artery volume, among others, or a combination thereof.

In some embodiments, the boundary condition determination module 26 may be configured to determine boundary conditions for each boundary for each arterial segment. By way of example, the boundary conditions for each segment may include inflow boundary conditions, outflow boundary conditions, one or more vessel wall boundary conditions, among others, or a combination thereof. The inflow boundary condition may be a value or a range of values for velocity, flow rate, pressure or other characteristics. Each outflow boundary condition may be a value or a range of values for velocity, flow rate, pressure, a percentage of inflow boundary, or other characteristic. Each vessel wall boundary condition may be a value or a range of values for velocity, flow rate, pressure, a combination thereof, or other characteristic.

In some embodiments, the determination of the inflow boundary condition and/or outflow boundary conditions may be determined based on patient information, an applicable physiological state (e.g., resting state, hyperemic state), the type of segment (e.g., LCA or RCA), among others, or a combination thereof. In some embodiments, the inflow boundary condition may be determined according to an expected patient activity level (e.g., according to information provided by the patient). In some embodiments, the inflow boundary condition may be a stored value and/or specified by the user.

In some embodiments, an inflow boundary condition may be determined according to the geometry of the anatomical ROI, such as the radius, diameter, length, or volume of a vessel portion (e.g., epicardial coronary artery volume). For example, the flow rate may be calculated according to a model based on the lumen volume of the region of interest, as shown in equation 9 below:

$$Q_{in} = \alpha V^\beta \qquad (\text{Eq. 9})$$

where $Q_{in}$ is a flow rate at an inlet of the anatomical model, V is the lumen volume of the region of interest, $\alpha$ is a coefficient that depends on the physiologic state of the patient, and $\beta$ is a coefficient that depends on the vessel tree structure and, in some embodiments, resolution of the images used to generate the 3D model of the anatomical region.

In embodiments in which the region of interest is the coronary artery tree, V may be the lumen volume of the LCA or RCA defined from the proximal origin to a location where the segmented vessel diameter is a particular diameter, which diameter may depend on the resolution of the images used to create the model of the patient anatomical portion. For example, the location may be defined as the diameter of three or four voxels in the image data set, in some embodiments. In a particular example, the location may be where the lumen has a diameter of 1 mm or 1.5 mm.

In some embodiments, parameters $\alpha$ and $\beta$ may be constants across all patients and may be determined from an example data set having both noninvasive and invasive data from which the values of $\alpha$ and $\beta$ may be validated.

In some embodiments, the outflow boundary conditions may be determined using an outflow distribution model. The outflow distribution model may be determined using geometrical data and/or stored hemodynamic data. The stored hemodynamic data may define or be used to define an empirical relationship between geometry (e.g., radii, diameters, lengths, volumes, etc.) of outflow boundaries and respective flow rates. For example, the boundary condition generation module can determine the outflow distribution model using stored hemodynamic data and the radii, diameters, lengths, volumes, etc. of the first and second outflow boundaries of the segment. In another example, the boundary condition generation module can determine the outflow distribution model using only geometrical data, for example, the radius, diameter, length, volume, etc. of the first outflow boundary (the distal boundary) of the segment or vessel portion proximate the boundary. The outflow distribution model can be used to determine outflow (e.g., velocity, flow rate, percentage of inflow) for each outflow boundary, thereby determining each outflow boundary condition.

By way of example, the boundary conditions determined by the boundary condition determination module 26 can be used with steady and/or unsteady flow computations to determine flow field (e.g., blood flow, wall shear stress, etc.) and hemodynamic information (e.g., FFR, IWFR, etc.). The boundary condition determination module also uses an optimization approach to define the artery segment flow splitting. Therefore, the boundary condition generation module 26 can provide flexibility, accuracy, and efficiency in determining the boundary conditions.

The flow field determination module 28 may be configured to determine a flow field for each arterial segment using the geometrical representation determined by the geometry determination module 24, the one or more boundary conditions determined by the boundary condition determination module 26, and pressure data respective of the patient. The pressure data may be, for example, a cuff pressure of the patient at a state of rest. In some embodiments, the flow field may include but is not limited to pressure field, velocity field, wall shear stress field, axial plaque stress, among others, or a combination thereof.

In some embodiments, a flow field parameter (e.g., pressure field, velocity, etc.) may be based on only the geometrical data and boundary conditions. This way, the flow field determination module may be configured to determine the flow field based only spatial location (i.e., independent of time).

The pressure determination module 30 may be configured to determine blood pressure at one or more points in a patient anatomy using the flow field determined by the flow field determination module 28. In some embodiments, the pressure data can be determined from a computed flow/pressure field, a non-invasive determination of a mean blood pressure of the patient, for example, determined by a blood pressure cuff, among others, or a combination thereof.

The pressure determination module 30 may be configured to determine a specific pressure at a specific location in the patient's anatomy responsive to a user (e.g., physician) selection of the specific location. The user may enter that selection with the user input device 14 relative to a display of the geometric model of the patient region of interest (e.g., arteries) on the display 18. In embodiments, the pressure determination module may be configured to determine pressures up- and/or downstream from the user-selected location, so as to determine a pressure drop at the user-selected location.

The hemodynamic information computing system 32 may be configured to calculate one or more hemodynamic parameters respective of a patient, such as IWFR or dPR, for example. Calculating a patient's IWFR may include, for example, calculating a range of pressure drops for one or more points in a patient's anatomy for a range of flow rates, in some embodiments. In other embodiments, calculating a patient's IWFR, dPR or other diastolic index may include calculating a single pressure drop using an average flow rate for some or all of diastole (e.g., the wave-free period of diastole). Based on the IWFR value calculated for the patient, it can be determined by the system 16 or by a clinician whether further diagnostic procedures and/or interventional procedures should be performed.

Figure 2:
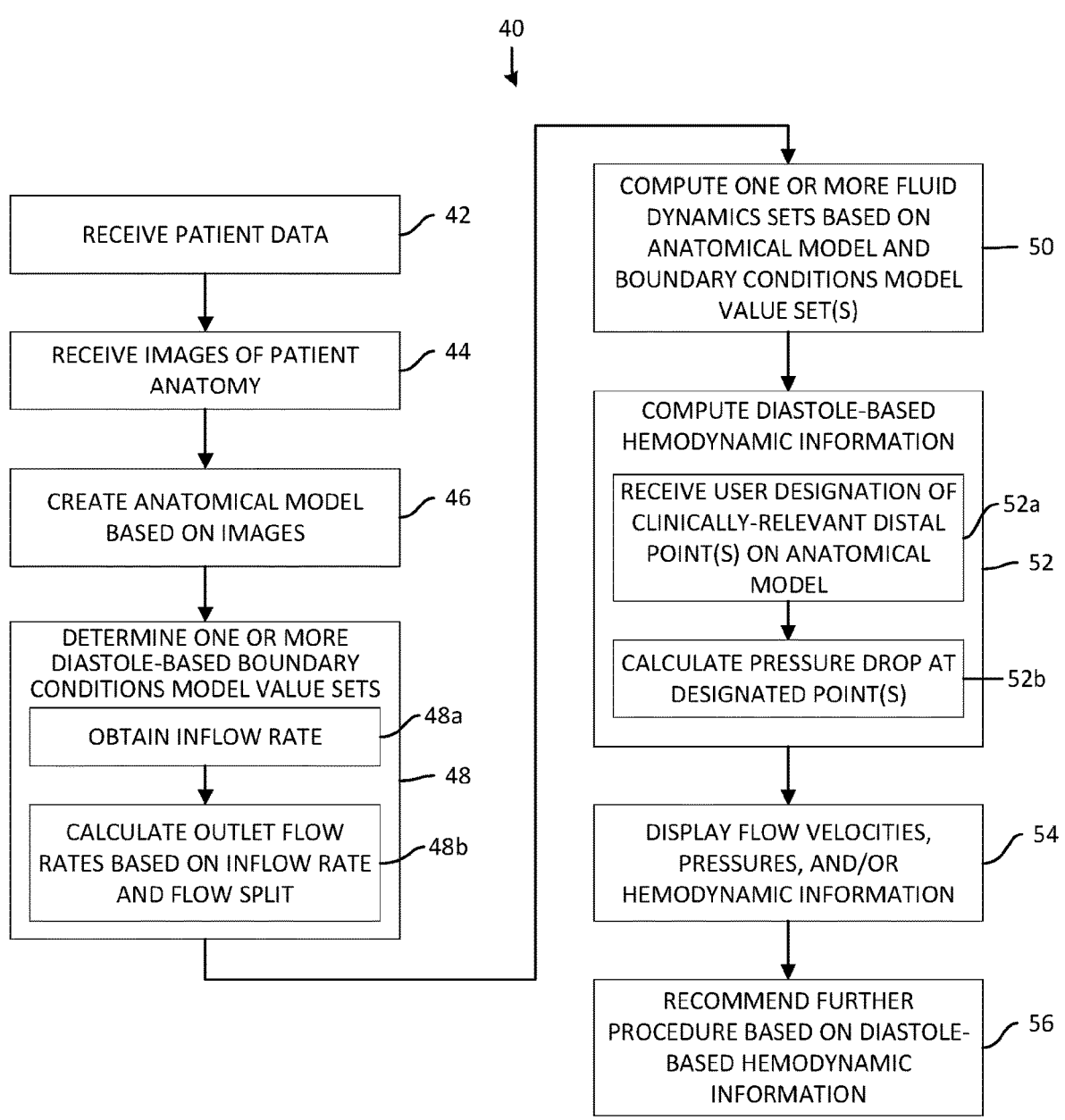
FIG. 2 is a flow chart illustrating an example embodiment of a method for determining hemodynamic information of a patient based on electronic patient data.

FIG. 2 is a flow chart illustrating an example embodiment of a method 40 for determining hemodynamic information for a patient. The method 40, or one or more aspects of the method 40, may be performed by the hemodynamic information computing system 16 of FIG. 1, in embodiments.

The method 40 may include, at block 42, receiving patient data. The patient data may include, for example, basic information about the patient, such as the patient's age, gender, brachial cuff blood pressure, a description of user symptoms, etc. The patient data may further include, in embodiments, metabolic data of the patient, such as a user's typical activity level (e.g., sedentary or active, amount of exercise per week, amount of specific activities per week, such as walking and running, etc.). The patient data may further include, in an embodiment, patient data from one or more diagnostic tests, such as echocardiography.

The method 40 may further include, at block 44, receiving images of the patient anatomy. The received patient images may be CT images, MRI images, or other noninvasively-obtained images, in embodiments. The images may include an anatomical region of interest of the patient. In an embodiment, for example, the received images may include one or more coronary arteries or other vasculature of interest. The images may be received from a patient image source, such as an imaging device or a database or other computer memory.

Figure 5:
FIG. 5 illustrates an example geometric model of a patient anatomical region that may be determined and find use with the methods of the present disclosure.

The method 40 may further include, at block 46, creating an anatomical model respective of the patient region of interest based on the images received at block 44. In an embodiment, the anatomical model may be created by segmenting the anatomy of interest from the images received at block 44. The anatomy of interest may be, for example, one or more coronary arteries. FIG. 5 illustrates an example anatomical model 58 of coronary arteries. The anatomical model may be created by the geometry determination module 24 of FIG. 1, in an embodiment. In some embodiments, an anatomical model may be obtained by a computing system (e.g., the hemodynamic information computing system 16) by being created by the computing system, or by receiving an existing model of the subject patient.

The method 40 may further include, at block 48, determining one or more diastole-based boundary conditions model value sets. The one or more boundary conditions value sets may be respective sets of values for the same boundary conditions model, in an embodiment (e.g., respective sets of condition values for the same inflow boundaries, outflow boundaries, wall boundaries, etc.). Block 48 may include sub-parts 48a and 48b, in some embodiments. Accordingly, the method 40 may include, at block 48a, obtaining an inflow rate. The inflow rate may be a flow rate for an inlet of the anatomical ROI of the patient, in some embodiments. In other embodiments, the blood flow rate may be a flow rate for another portion of the ROI.

The inflow rate obtained at block 48a may be representative of a particular physiologic state of the patient. For example, in some embodiments, the inflow rate obtained at block 48a may be representative of a resting state of the patient.

The inflow rate obtained at block 48a may be representative of a desired point or portion of the cardiac cycle of the patient, in some embodiments. For example, in some embodiments, the inflow rate obtained at block 48a may be representative of an average flow rate over the entire wave-free period of diastole of the patient. In other embodiments, the inflow rate may be representative of an average flow rate of the entirety of diastole of the patient. In other embodiments, the inflow rate may be representative of the particular time point within diastole, such as the midpoint of diastole.

In some embodiments, obtaining the inflow rate at block 48a may include calculating an inflow rate according to a geometry of the patient anatomical model as discussed with respect to equation (9) above. In an embodiment, the value of a selected for the inflow rate may be representative of a particular period or time point in the cardiac cycle (e.g., the beginning of diastole, the end of diastole, the beginning of the wave-free period of diastole, the end of the wave-free period of diastole, etc.).

In other embodiments, instead of calculating an inflow rate according to equation 9 above, obtaining a blood flow rate at block 48a may include receiving a user input of an inflow rate. The inflow rate may be received via user manual entry (e.g., with the user input device 14 of the system 10). In an embodiment, the inflow rate at block 48a may be determined (e.g., by a clinician or by an electronic system) based on the metabolic demands and condition of the patient.

Block 48 may further include, at block 48b, calculating outlet flow rates according to the inflow rate obtained at block 48a and according to a flow splitting model. The flow splitting model may be, or may have been, calculated or otherwise determined according to a geometry of the three-dimensional electronic model of the patient anatomical region. The flow splitting model may be calculated according to the relative radii, diameters, circumferences, lengths, volumes, and/or surface areas of the vessels in the electronic model, in some embodiments.

In conjunction with the flow rate obtained in block 48a, the outlet flow rates calculated at block 48b may be comprise a boundary condition model of the patient anatomical region. The boundary condition model may therefore be representative of a particular physiologic state of the patient (e.g., a resting state) and a particular portion or point in the cardiac cycle of the patient (e.g., the entire diastolic period, the wave-free portion of diastole, a time point in diastole, etc.).

In embodiments in which the anatomical region is a coronary artery of the patient, the inflow rate obtained at block 48a may be an inlet flow rate for the coronary artery, and the flow splitting model may be calculated according to the geometry of the coronary artery portions downstream of the inlet in the electronic model. The flow splitting model may be calculated according to the relative radii, diameters, circumferences, lengths, surface areas, or volumes of the coronary artery portions downstream of the inlet. In some embodiments, the flow splitting model may be calculated according to the epicardial coronary artery volume of the electronic model.

The method 40 may further include, at block 50, computing one or more fluid dynamics flow fields of the blood flow through the patient anatomy based on the anatomical model (e.g., model 58), the one or more boundary conditions model value sets, and, in some embodiments, the patient data. Block 50 may include determining the flow field for each arterial segment using the anatomical model, boundary conditions, and pressure data respective of the patient (e.g., aortic pressure data). In some embodiments, the pressure data may be obtained for the patient, for example, cuff pressure, and/or may be a stored value. In some embodiments, the flow field may include but is not limited to pressure field, velocity field, among others, or a combination thereof. The fluid dynamics may be computed by the flow field determination module 28 of FIG. 1, in an embodiment.

In some embodiments, the velocity field and/or pressure field may be determined based only on the boundaries and the boundary conditions, without regard to time. For example, the velocity field and/or pressure field may be determined using a steady flow Navier-Stokes equation in which the velocity and pressure variables are functions of only spatial location (i.e., time is not considered). This way, pressure and velocity can be accurately and efficiently determined in near real-time so as to enable point of care analysis by the clinician.

The method 40 may further include, at block 52, computing diastole-based hemodynamic information respective of the patient based on the patient data and the computed fluid dynamics. The hemodynamic information may be or may include a diastole-based index, such as IWFR, in an embodiment. Computing IWFR may include calculating one or more pressure drops for one or more locations in the patient's vasculature. The set of pressure drops can be analyzed relative to aortic pressure during diastole to determine the hemodynamic index value.

Block 52 may include, at block 52a, receiving a user designation of one or more clinically-relevant distal points on an anatomical model of the patient. For example, a user may enter, with a user input device, an annotation of one or more distal points on an anatomical model of the patient's vasculature, and the hemodynamic information computing system may thereby receive the one or more annotations from the user. The indicated points may be one or more locations distal to a suspected stenosis in the coronary arteries, for example.

Block 52 may further include, at block 52b, calculating a respective pressure drop at each of the user-designated points for a first cardiac cycle state. The first state may be, for example, the beginning of diastole. The pressure drop may be calculated based on a flow field calculated for the first cardiac cycle state at the one or more user-designated points. The remaining aspects of the method 80 may be performed for each indicated point to determine if that point is likely to have a clinically-significant stenosis, in an embodiment.

The method 60 may further include, at block 54, displaying the flow velocities, pressures, and/or hemodynamic information. The display may include, for example, one or more indicators of flow velocities, pressures, and/or hemodynamic information at one or more locations in the patient's vasculature, overlaid on or presented adjacent to the geometric model of the patient anatomy.

The method 40 may further include, at block 56, recommending a further procedure for the patient based on the computed hemodynamic information. For example, if the hemodynamic information is below a threshold that indicates a stenosis is present in the patient's vasculature, then a further diagnostic procedure may be recommended for the patient, such as an invasive angiography and pressure measurement at the site of the suspected stenosis. Additionally or alternatively, a corrective procedure may be recommended to address the stenosis, such as placement of a stent at the location of the suspected stenosis, for example.

Figure 3:
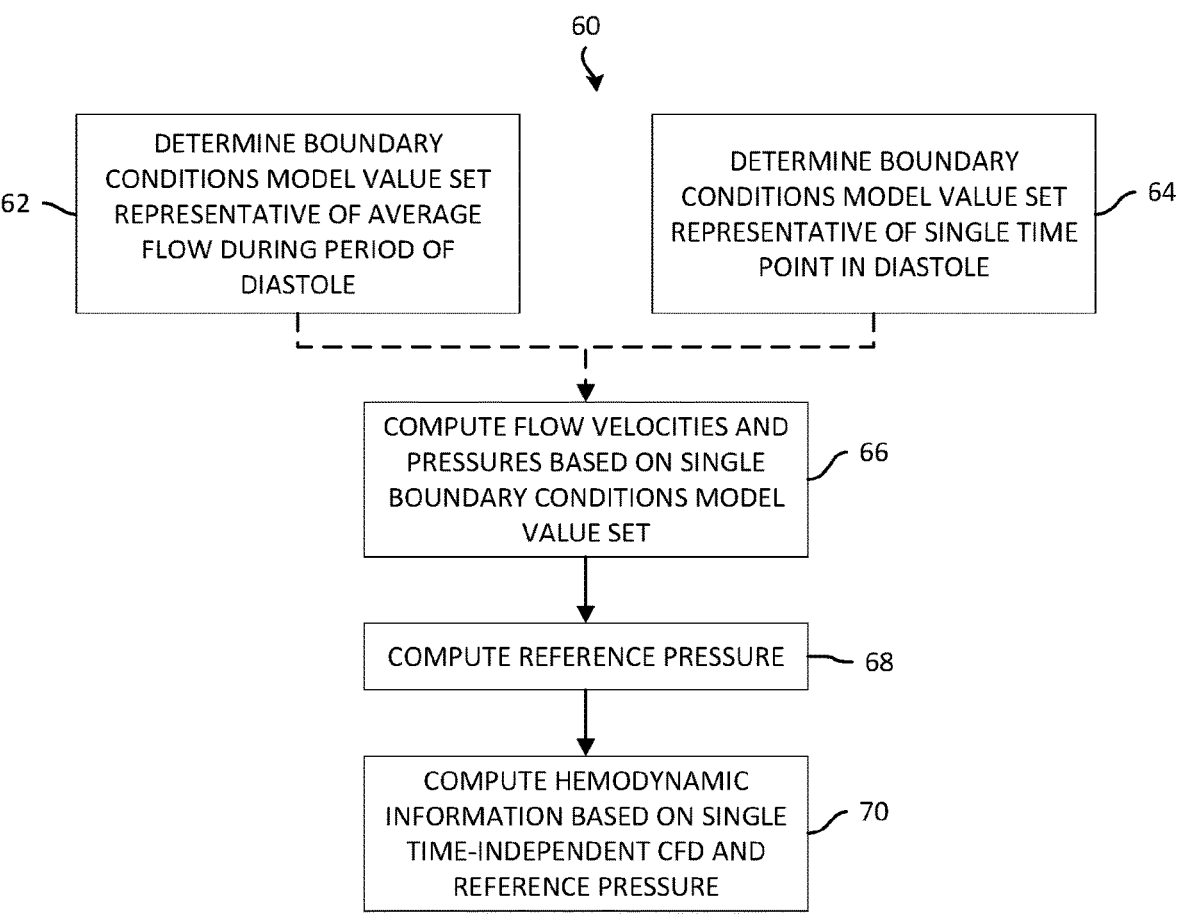
FIG. 3 is a flow chart illustrating an example embodiment of a method for determining hemodynamic information based on a single value set of a boundary conditions model representative of a single time point in the cardiac cycle or average flow conditions of a portion of the cardiac cycle.

FIG. 3 is a flow chart illustrating an example embodiment of a method 60 for determining hemodynamic information based on a single value set of a boundary conditions model representative of a single time point in the cardiac cycle or average flow conditions of a portion of the cardiac cycle. The method 60, or one or more aspects of the method 60, may be performed by the hemodynamic information computing system 16 of FIG. 1, in embodiments. The method 60 may be considered an embodiment of blocks 48, 50, and 52 of the method 40.

The method 60 may include, at block 62, determining a boundary conditions model value set representative of average flow conditions during a period of diastole. For example, in an embodiment, block 62 may include determining a boundary conditions model value set representative of average flow for the entirety of diastole. In another embodiment, block 62 may include determining a boundary conditions model value set representative of the wave-free period of diastole. A boundary conditions model may be determined as discussed with respect to block 48 of the method 40, in some embodiments.

The method 60 may further include, at block 64, determining a boundary conditions model value set representative of a single time point of diastole, such as the midpoint of diastole. A boundary conditions model value set may be determined as discussed with respect to block 48 of the method 40, in some embodiments.

One or both of block 62 or block 64 may be performed, in embodiments, according to the desired hemodynamic index desired for calculation. For example, if an IWFR calculation is desired, block 62 may be performed with respect to the wave-free period of diastole; if a dPR calculation is desired, block 62 may be performed with respect to the entirety of diastole; if a dPR calculation is desired, block 64 may be performed with respect to the midpoint of diastole.

The method 60 may further include, at block 66, computing flow velocities and pressure based on a single boundary conditions model value set (e.g., either of block 62 or 64). Flow velocities may be calculated at block 66 in a single time-independent CFD simulation. For example, the velocity field and/or pressure field may be determined using steady flow Navier-Stokes equations in which the velocity and pressure variables are functions of only spatial location (i.e., time is not considered). The flow velocities and pressures may be determined, for example, by the flow field determination module 28 of the system 10 of FIG. 1. In embodiments, multiple instances of block 66 may be implemented, each of which may result in a separate hemodynamic index calculation.

The method 60 may further include, at block 68, computing a reference pressure. The reference pressure may be an aortic pressure, in some embodiments. As disclosed herein, one or more aortic pressures may be determined based on cuff pressures respective of the patient. The aortic pressures may be aortic pressures for the beginning, end, and/or mid-diastole, in an embodiment. The reference pressure calculated at block 68 may be representative of the same point or portion of the cardiac cycle as the boundary conditions model value set used as the basis for the calculations at block 66.

The method 60 may further include, at block 70, computing hemodynamic information based on a single time-independent CFD of block 66 and the reference pressure of block 68. The hemodynamic information may be or may include a hemodynamic index value. In an embodiment, the hemodynamic index value may be an IWFR value. The index value may be an average of the ratio of local pressure to aortic pressure over diastole, in an embodiment, in which the local pressure is determined by the computed pressure field at locations of interest, such as distal to a stenosis.

Figure 4:
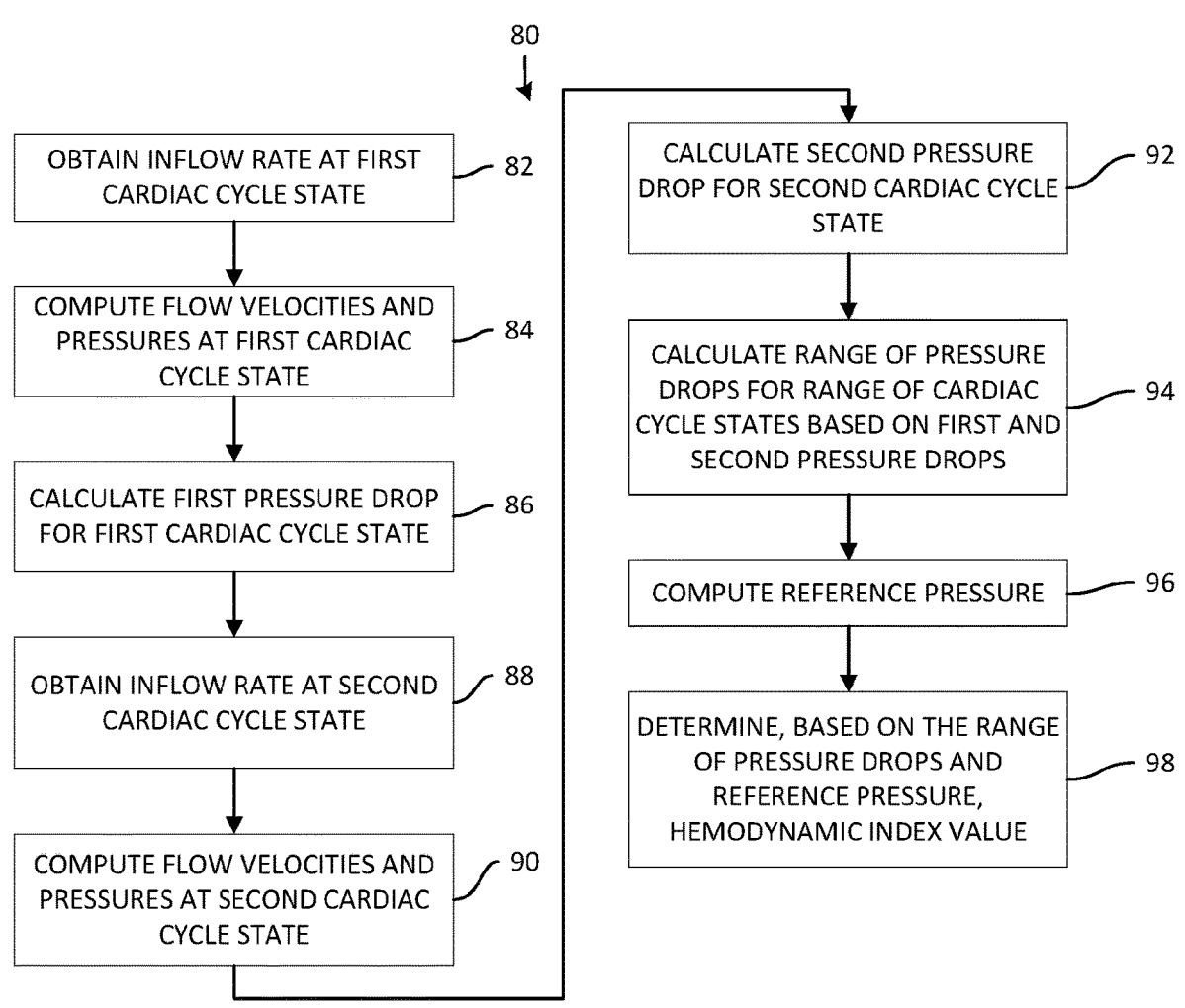
FIG. 4 is a flow chart illustrating an embodiment of a method for determining hemodynamic information based on two boundary conditions model value sets representative of two different cardiac cycle states.

FIG. 4 is a flow chart illustrating an embodiment of a method 80 for determining hemodynamic information based on two boundary conditions model value sets representative of two different cardiac cycle states. The method 80, or one or more aspects of the method 80, may be performed by the hemodynamic information computing system 16 of FIG. 1, in embodiments. The method 80 may be considered an embodiment of blocks 48, 50, and 52 of the method 40.

The method 80 may include, at block 82, obtaining an inflow rate at a first cardiac cycle state of the patient. The first blood flow rate may be an expected flow rate for the patient at the beginning of diastole, for example. The flow rate at block 62 may be received via user manual entry of the flow rate (e.g., with the user input device 14 of the system 10). In an embodiment, the flow rate at block 62 may be determined (e.g., by a clinician or by an electronic system) based on the metabolic demands and condition of the patient.

The method 80 may further include, at block 84, computing flow velocities and pressures in the region of interest at the first cardiac cycle state of the patient. The first cardiac cycle state may be the beginning of diastole, for example. In some embodiments, the velocity field and/or pressure field may be determined based on defined boundaries and boundary conditions (which may, in turn, be based on the flow rate received at block 82) respective of the region of interest.

The method 80 may further include, at block 86, calculating a first pressure drop (e.g., at one or more user-designated points and/or other points) for the first cardiac cycle state. The pressure drop may be a drop in pressure from the vessel inlet to a relevant point (e.g., user-designated or otherwise). The first state may be, for example, the beginning of diastole. The pressure drop may be calculated based on a flow field calculated for the first cardiac cycle state.

The method 80 may further include, at block 88, obtaining an inflow rate at a second cardiac cycle state of the patient that is different from the first cardiac cycle state. The second inflow rate may be an expected flow rate for the patient at the end of diastole, for example. The flow rate at block 88 may be received via user manual entry of the flow rate (e.g., with the user input device 14 of the system 10). In an embodiment, the inflow rate at block 88 may be determined (e.g., by a clinician or by an electronic system) based on the metabolic demands and condition of the patient.

The method 80 may further include, at block 90, computing flow velocities and pressures in the region of interest at the second cardiac cycle state of the patient. The flow velocities and pressures may be computed substantially as described above with respect to block 84, but with the boundary conditions determined according to the second blood flow rate.

The method 80 may further include, at block 92, calculating a second pressure drop at one or more points for the second cardiac cycle state. The second cardiac cycle state may be, for example, the end of diastole. The pressure drop may be calculated based on a flow field calculated for the second cardiac cycle state at the one or more user-designated points.

The method 94 may further include calculating a range of pressure drops at the relevant (e.g., user-designated) points for a range of cardiac cycle states based on the first and second pressure drops. The range of pressure drops may be calculated for a range of cardiac cycle states, from (or across) $Q_1$ to $Q_2$, where $Q_1$ is the inflow rate at the first cardiac cycle state and $Q_2$ is the inflow rate at the second cardiac cycle state. The pressure drop for a given flow rate may be calculated according to a quadratic equation, shown as equation (1) in this disclosure and repeated below:

$$\Delta P = aQ + bQ^2$$

where Q is the flow rate at the given cardiac cycle state, and a and b are patient-specific constants. As described above, in order to compute a and b, three-dimensional Navier-Stokes equations can be solved for two values of Q (e.g., flow rates at first and second cardiac cycle states), as discussed herein with respect to equations (2) and (3). Once coefficients a and b are known, $\Delta P$ may be calculated over diastole without requiring CFD for each time point in diastole. That range of $\Delta P$ may then be used to compute an average value to determine a hemodynamic index, in embodiments, such as IWFR.

Figure 6:
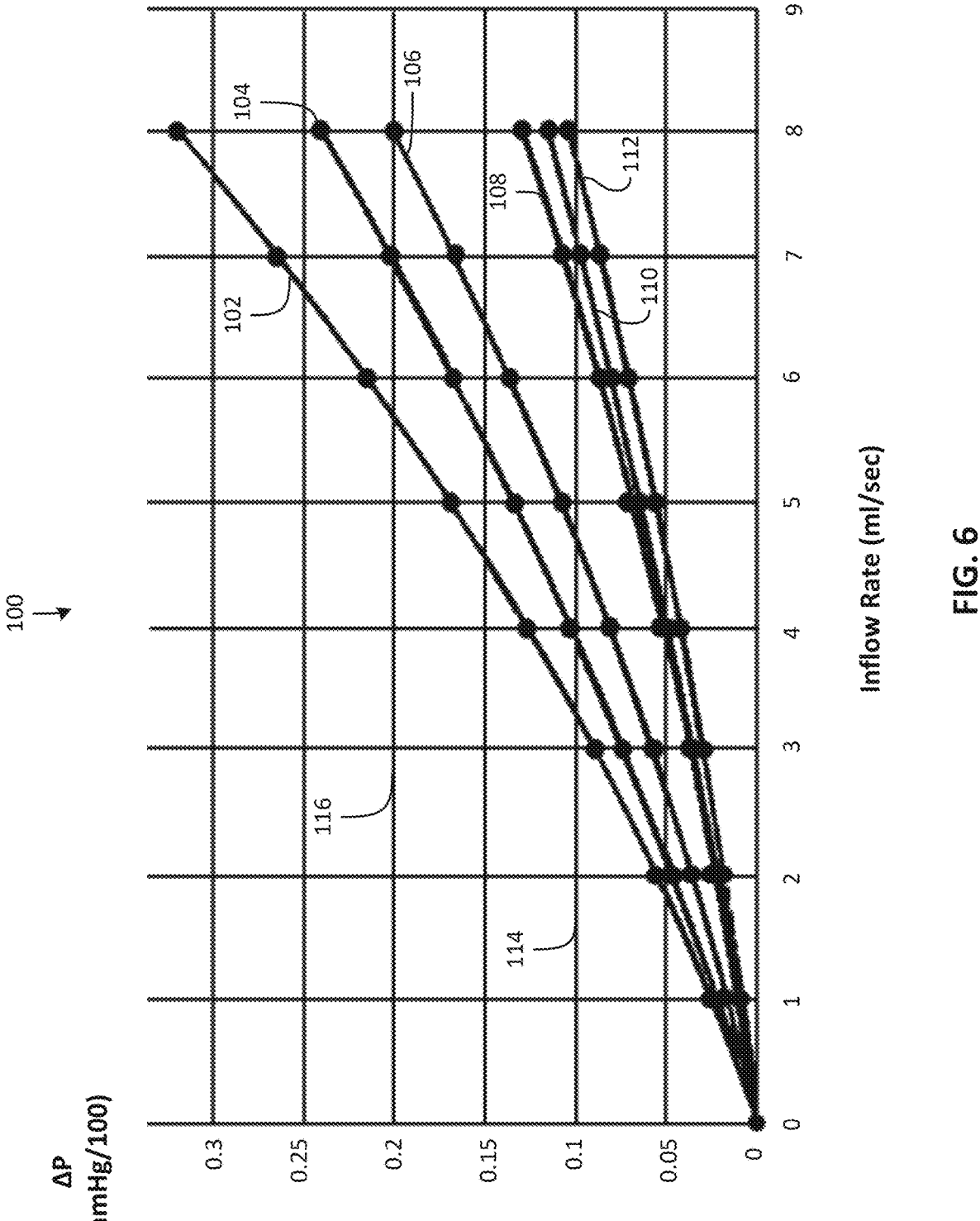
FIG. 6 is a plot illustrating example ranges of pressure drops for example ranges of flow rates for a set of patients.

FIG. 6 is a plot 100 illustrating example ranges of pressure drops for example ranges of activity levels for a set of patients. The plot 100 of FIG. 6 includes pressure drop (in mmHg/100) on the vertical axis and flow rate (in ml/sec) on the horizontal axis, with six plot lines 102, 104, 106, 108, 110, 112 respective of six patients shown, and two horizontal threshold lines 114, 116 shown. The first threshold line 114 may be generally indicative of a clinically-significant pressure drop for hyperemic blood flow. The second threshold line 116 may be generally indicative of a clinically-significant pressure drop for resting flow.

As a result of the method 80, a flow field and/or pressure field may be calculated (and, in embodiments, displayed or otherwise output) for one or more locations in a patient's vasculature, for one or more cardiac cycle states of the patient. For example, in an embodiment, flow fields and pressure fields may be calculated and output for the beginning and end of diastole. Such flow fields may be used to determine hemodynamic information respective of the patient such as, for example, an IWFR value or other diastole-based hemodynamic value.

The method 80 may further include, at block 96, determining a reference pressure, such as one or more aortic pressures. The aortic pressures may be determined based on cuff pressures respective of the patient, as described herein. The aortic pressures may be aortic pressures for the beginning, end, and/or mid-diastole, in an embodiment. In some embodiments, the reference pressure calculated at block 96 may be representative of a portion of the cardiac cycle that spans the first and second cardiac cycle states of blocks 82, 84, 86, 88, 90, 92.

The method 80 may further include, at block 98, determining, based on the range of pressure drops and reference pressure, a hemodynamic index value. In an embodiment, the hemodynamic index value may be an IWFR value. The index value may be an average of the ratio of local pressure to aortic pressure over diastole, in an embodiment, in which the local pressure is determined by the computed pressure field at locations of interest, such as distal to a stenosis. In an embodiment, a pressure v. flow rate curve for diastole (e.g., as illustrated in FIG. 6) may be integrated and averaged to calculate an IWFR value. For example, referring to FIG. 6, a given plot line (e.g., plot line 104) may be integrated and averaged in order to calculate an IWFR value for the patient associated with the plot line 104.

Figure 7:
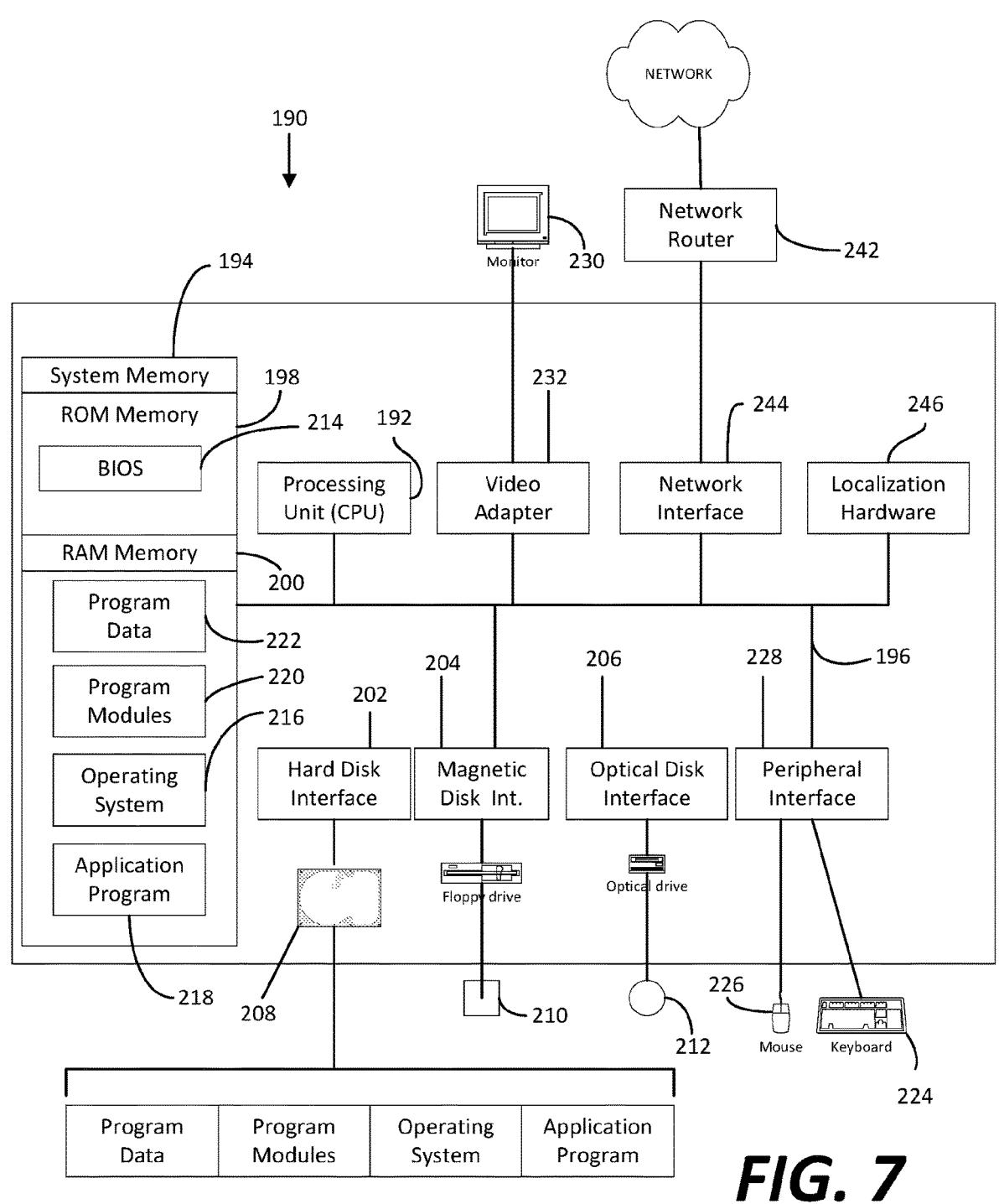
FIG. 7 is a diagrammatic view of an example embodiment of a user computing environment.

FIG. 7 is a diagrammatic view of an example embodiment of a user computing environment that includes a general purpose computing system environment 190, such as a desktop computer, laptop, smartphone, tablet, or any other such device having the ability to execute instructions, such as those stored within a non-transient, computer-readable medium. Furthermore, while described and illustrated in the context of a single computing system 190, those skilled in the art will also appreciate that the various tasks described hereinafter may be practiced in a distributed environment having multiple computing systems 190 linked via a local or wide-area network in which the executable instructions may be associated with and/or executed by one or more of multiple computing systems 190. The computing environment 190, or portions thereof, may comprise the system 10 of FIG. 1, in embodiments.

In its most basic configuration, computing system environment 190 typically includes at least one processing unit 192 and at least one memory 194, which may be linked via a bus 196. Depending on the exact configuration and type of computing system environment, memory 194 may be volatile (such as RAM 200), non-volatile (such as ROM 198, flash memory, etc.) or some combination of the two. Computing system environment 190 may have additional features and/or functionality. For example, computing system environment 190 may also include additional storage (removable and/or non-removable) including, but not limited to, magnetic or optical disks, tape drives and/or flash drives. Such additional memory devices may be made accessible to the computing system environment 190 by means of, for example, a hard disk drive interface 202, a magnetic disk drive interface 204, and/or an optical disk drive interface 206. As will be understood, these devices, which would be linked to the system bus 196, respectively, allow for reading from and writing to a hard disk 208, reading from or writing to a removable magnetic disk 210, and/or for reading from or writing to a removable optical disk 212, such as a CD/DVD ROM or other optical media. The drive interfaces and their associated computer-readable media allow for the nonvolatile storage of computer readable instructions, data structures, program modules and other data for the computing system environment 190. Those skilled in the art will further appreciate that other types of computer readable media that can store data may be used for this same purpose. Examples of such media devices include, but are not limited to, magnetic cassettes, flash memory cards, digital videodisks, Bernoulli cartridges, random access memories, nanodrives, memory sticks, other read/write and/or read-only memories and/or any other method or technology for storage of information such as computer readable instructions, data structures, program modules or other data. Any such computer storage media may be part of computing system environment 190.

A number of program modules may be stored in one or more of the memory/media devices. For example, a basic input/output system (BIOS) 214, containing the basic routines that help to transfer information between elements within the computing system environment 190, such as during start-up, may be stored in ROM 198. Similarly, RAM 200, hard drive 208, and/or peripheral memory devices may be used to store computer executable instructions comprising an operating system 216, one or more applications programs 218 (such as the modules 24, 26, 28, 30, 32 of FIG. 1), other program modules 220, and/or program data 222. Still further, computer-executable instructions may be downloaded to the computing environment 190 as needed, for example, via a network connection.

An end-user, e.g., a clinician, may enter commands and information into the computing system environment 190 through input devices such as a keyboard 224 and/or a pointing device 226. While not illustrated, other input devices may include a microphone, a joystick, a game pad, a scanner, etc. These and other input devices would typically be connected to the processing unit 192 by means of a peripheral interface 228 which, in turn, would be coupled to bus 196. Input devices may be directly or indirectly connected to processor 192 via interfaces such as, for example, a parallel port, game port, firewire, or a universal serial bus (USB). To view information from the computing system environment 190, a monitor 230 or other type of display device may also be connected to bus 196 via an interface, such as via video adapter 232. In addition to the monitor 230, the computing system environment 190 may also include other peripheral output devices, not shown, such as speakers and printers.

The computing system environment 190 may also utilize logical connections to one or more computing system environments. Communications between the computing system environment 190 and the remote computing system environment may be exchanged via a further processing device, such a network router 242, that is responsible for network routing. Communications with the network router 242 may be performed via a network interface component 244. Thus, within such a networked environment, e.g., the Internet, World Wide Web, LAN, or other like type of wired or wireless network, it will be appreciated that program modules depicted relative to the computing system environment 190, or portions thereof, may be stored in the memory storage device(s) of the computing system environment 190.

The computing system environment 190 may also include localization hardware 186 for determining a location of the computing system environment 190. In embodiments, the localization hardware 246 may include, for example only, a GPS antenna, an RFID chip or reader, a WiFi antenna, or other computing hardware that may be used to capture or transmit signals that may be used to determine the location of the computing system environment 190.

While this disclosure has described certain embodiments, it will be understood that the claims are not intended to be limited to these embodiments except as explicitly recited in the claims. On the contrary, the instant disclosure is intended to cover alternatives, modifications and equivalents, which may be included within the spirit and scope of the disclosure. Furthermore, in the detailed description of the present disclosure, numerous specific details are set forth in order to provide a thorough understanding of the disclosed embodiments. However, it will be obvious to one of ordinary skill in the art that systems and methods consistent with this disclosure may be practiced without these specific details. In other instances, well known methods, procedures, components, and circuits have not been described in detail as not to unnecessarily obscure various aspects of the present disclosure.

Some portions of the detailed descriptions of this disclosure have been presented in terms of procedures, logic blocks, processing, and other symbolic representations of operations on data bits within a computer or digital system memory. These descriptions and representations are the means used by those skilled in the data processing arts to most effectively convey the substance of their work to others skilled in the art. A procedure, logic block, process, etc., is herein, and generally, conceived to be a self-consistent sequence of steps or instructions leading to a desired result. The steps are those requiring physical manipulations of physical quantities. Usually, though not necessarily, these physical manipulations take the form of electrical or magnetic data capable of being stored, transferred, combined, compared, and otherwise manipulated in a computer system or similar electronic computing device. For reasons of convenience, and with reference to common usage, such data is referred to as bits, values, elements, symbols, characters, terms, numbers, or the like, with reference to various presently disclosed embodiments.

It should be borne in mind, however, that these terms are to be interpreted as referencing physical manipulations and quantities and are merely convenient labels that should be interpreted further in view of terms commonly used in the art. Unless specifically stated otherwise, as apparent from the discussion herein, it is understood that throughout discussions of the present embodiment, discussions utilizing terms such as "determining" or "outputting" or "transmitting" or "recording" or "locating" or "storing" or "displaying" or "receiving" or "recognizing" or "utilizing" or "generating" or "providing" or "accessing" or "checking" or "notifying" or "delivering" or the like, refer to the action and processes of a computer system, or similar electronic computing device, that manipulates and transforms data. The data is represented as physical (electronic) quantities within the computer system's registers and memories and is transformed into other data similarly represented as physical quantities within the computer system memories or registers, or other such information storage, transmission, or display devices as described herein or otherwise understood to one of ordinary skill in the art.

What is claimed is:

1. A method for providing hemodynamic information respective of a patient, the method comprising:
  obtaining a three-dimensional electronic model of a coronary artery of the patient;
  obtaining a boundary condition model value set that is specific to a midpoint of a diastole period of the patient's cardiac cycle at a resting state of the patient, wherein the boundary condition model value set comprises at least one inflow rate at a boundary of the three-dimensional model and at least one outflow rate at a boundary of the three-dimensional model;
  performing a three-dimensional computational fluid dynamics (CFD) simulation of the coronary artery model based on the boundary condition model;
  calculating, according to the CFD simulation, a pressure drop between a first location of the coronary artery and a second location of the coronary artery; and
  determining, based on the calculated pressure drop and based on a reference pressure, a hemodynamic index value indicative of the presence of a lesion at the location.

2. The method of claim 1, further comprising:
  creating the electronic model of the coronary artery.

3. The method of claim 2, further comprising:
  receiving image data respective of the coronary artery; and
  creating the electronic model based on the received image data.

4. The method of claim 1, wherein the boundary condition model value set comprises:

an inlet flow rate at an inlet of the coronary artery that is representative of a resting state of the patient; and two or more outlet flow rates calculated according to the inlet flow rate and a flow splitting model.

5. The method of claim 4, further comprising:

determining the flow splitting model according to a geometry of the three dimensional model of the coronary artery; and calculating the two or more outlet flow rates according to the inlet flow rate and the flow splitting model.

6. A system for providing hemodynamic information respective of a patient, the system comprising:

a non-transitory, computer-readable memory storing instructions; and a processor configured to execute the instructions to:

obtain a three-dimensional electronic model of a coronary artery of the patient;

obtain a boundary condition model value set that is specific to a midpoint of a diastole period of the patient's cardiac cycle at a resting state of the patient, wherein the boundary condition model value set comprises at least one inflow rate at a boundary of the three-dimensional model and at least one outflow rate at a boundary of the three-dimensional model;

perform a three-dimensional computational fluid dynamics (CFD) simulation of the coronary artery model based on the boundary condition model;

calculate, according to the CFD simulation, a pressure drop between a first location of the coronary artery and a second location of the coronary artery; and determine, based on the calculated pressure drop and based on a reference pressure, a hemodynamic index value indicative of the presence of a lesion at the location.

7. The system of claim 6, wherein the memory stores further instructions that, when executed by the processor, cause the processor to:

create the electronic model of the coronary artery.

8. The system of claim 7, wherein the memory stores further instructions that, when executed by the processor, cause the processor to:

receive image data respective of the coronary artery; and create the electronic model based on the received image data.

9. The system of claim 6, wherein the boundary condition model value set comprises:

an inlet flow rate at an inlet of the coronary artery that is representative of a resting state of the patient; and two or more outlet flow rates calculated according to the inlet flow rate and a flow splitting model.

10. The system of claim 9, wherein the memory stores further instructions that, when executed by the processor, cause the processor to:

determine the flow splitting model according to a geometry of the three dimensional model of the coronary artery; and calculate the two or more outlet flow rates according to the inlet flow rate and the flow splitting model.

11. A method for providing hemodynamic information respective of a patient, the method comprising:

obtaining a three-dimensional electronic model of an anatomical region of the patient;

obtaining a boundary condition model that is specific to a midpoint of a diastole period of the patient's cycle at a resting state of the patient, wherein the boundary condition model value set comprises at least one inflow rate at a boundary of the three-dimensional model and at least one outflow rate at a boundary of the three-dimensional model;

calculating, based on the three-dimensional model and the boundary condition model, at a first time point in a cardiac cycle of the patient, a first pressure drop across a portion of an anatomical region of a patient;

calculating, based on the three-dimensional model and the boundary condition model, at a second time point in a cardiac cycle of the patient that is different than the first time point, a second pressure drop across the anatomical region portion;

calculating, for a range of time points of the cardiac cycle of the patient, respective pressure drops across the region according to the first and second pressure drops; and determining, based on the calculated pressure drops for the range of time points and based on a reference pressure, a hemodynamic index value indicative of the presence of a lesion at the location.

12. The method of claim 11, wherein:

the anatomical region is a blood vessel; and the anatomical region portion extends from an inlet of the blood vessel to a location in the blood vessel.

13. The method of claim 12, wherein the anatomical region is a coronary artery.

14. The method of claim 11, further comprising:

receiving image data respective of the anatomical region of the patient; and creating the electronic model based on the received image data.

15. The method of claim 11, further comprising:

generating a curve of pressure relative to flow rate based on the pressure drops across the region; and integrating the plot line to calculate the hemodynamic index value.

* * * * *